United States Patent [19]

Devine et al.

[11] Patent Number: 5,728,551
[45] Date of Patent: Mar. 17, 1998

[54] IN VITRO TRANSPOSITION OF ARTIFICIAL TRANSPOSONS FOR DNA SEQUENCING

[75] Inventors: Scott E. Devine, Ellicott City; Jef D. Boeke; Lelita T. Braiterman, both of Baltimore, all of Md.

[73] Assignee: The Johns Hopkins University, Baltimore, Md.

[21] Appl. No.: 397,679

[22] Filed: Mar. 2, 1995

Related U.S. Application Data

[63] Continuation-in-part of Ser. No. 204,675, Mar. 2, 1994.
[51] Int. Cl.$^6$ ............................. C12N 9/00; C12N 15/66
[52] U.S. Cl. ................. 435/91.41; 435/6; 435/172.3; 435/183; 435/320.1; 536/25.3
[58] Field of Search .......................... 435/91.41, 320.1, 435/6, 172.3, 183; 536/23.7, 25.3

[56] References Cited

U.S. PATENT DOCUMENTS

| | | | |
|---|---|---|---|
| 5,137,829 | 8/1992 | Nag et al. | 435/320.1 |
| 5,212,080 | 5/1993 | Nag et al. | 435/172.3 |
| 5,227,288 | 7/1993 | Blattner | 435/6 |

FOREIGN PATENT DOCUMENTS

| | | |
|---|---|---|
| WO 90/00621 | 7/1989 | WIPO . |
| WO 92/03578 | 8/1991 | WIPO . |

OTHER PUBLICATIONS

Kasai et al. "Efficient Large-scale Sequencing of the *Escherichia coli* Genome: Implementation of a transposon- and PCR-based Strategy for the Analysis of Ofrdered lambda Phage Clones", Nucleic Acids Research, vol. 20, No. 24, pp. 6509-6515, 1992.
Eichinger et al. "A Specific Terminal Structure is Required For Ty1 Transposition", Genes and Development, vol. 4, pp. 324-330, 1990.
Dower et al. "High Efficiency Transformation by High Voltage Electroporation", Nucleic Acids Research, vol. 16, No. 13, pp. 6127-6145, 1988.
Methods in Enzymology, vol. 152, pp. 560-562, 1987.
High efficiency transformation of *E coli* by high voltege Electroporation Dower, W.J. et al (1988) Nucleic Acid Research vol. 16 No. 13,6127-6145.
Methods in enzymology (1987) vol. 152 pp. 560-562 Academic Press.
Kasai, et al., "Efficient Large-Scale Sequencing of the *Escherichia coli* Genome: Implementation of a Transposon- and PCR-Based Strategy for the Analysis of Ordered λPhage Clones", *Nucleic Acids Research*, 20(24):6509-6515 (1992).
Phadnis, et al., "Tn5supF, a 264-Base-Pair Transposon Derived from Tn5 for Insertin Mutagenesis and Sequencing DNAs Cloned in Phage λ", *Proc. Natl. Acad. Sci. USA*, 86:5908-5912 (1989).
Strathmann, et al., "Transposon-Facilitated DNA Sequencing", *Proc. Natl. Acad. Sci. USA*, 88:1247-1250 (1991).
Seifert, et al., "Shuttle Mutagensis: A Method of Transposon Mutagenesis for *Saccharomyces cerevisiae, Proc. Natl. Acad. Sci. USA*", 83:735-739 (1986).
Ahmed, "A Vector for Sequencing Long (40-kb) DNA Fragments", *Gene*, 75:315-321 (1988).
Way, et al., "New TN10 Derivatives for Transposon Mutagenesis and for Construction of *lacA* Operon Fusions by Transposition", *Gene*, 32:369-379 (1984).
Kleckner, et al., "Uses of Transposons with Emphasis on TN10", *Methods in Enzymology*, 204:139-180 (1991).
Eichinger, et al., "The DNA Intermediate in Yeast Ty1 Element Transposition Copurifies with Virus-Like Particles: Cell-Free Ty1 Transposition," *Cell*, 54:955-966 (1988).
Brown, et al., "Correct Integration of Retroviral DNA *in vitro*", *Cell*, 49:347-356 (1987).
Eichinger, et al., "A Specific Terminal Structure is Required for Ty1 Transposition", *Genes & Development*, 4:324-330 (1990).

*Primary Examiner*—Douglas W. Robinson
*Assistant Examiner*—Amy J. Nelson
*Attorney, Agent, or Firm*—Banner & Witcoff, Ltd.

[57] ABSTRACT

We have developed efficient methods of creating artificial transposons and inserting these transposons into DNA targets in vitro, primarily for the purpose of mapping and sequencing DNA. A target DNA has been engineered to convert virtually any DNA sequence, or combination of sequences, into an artificial transposon; hence, custom transposons containing any desired feature can be easily designed and constructed. Such transposons are then efficiently inserted into DNA targets, in vitro, using the integrase activity present in yeast Ty1 virus-like particles. Primers complementary to the transposon termini can be used to sequence DNA flanking any transposon insertion.

30 Claims, 18 Drawing Sheets

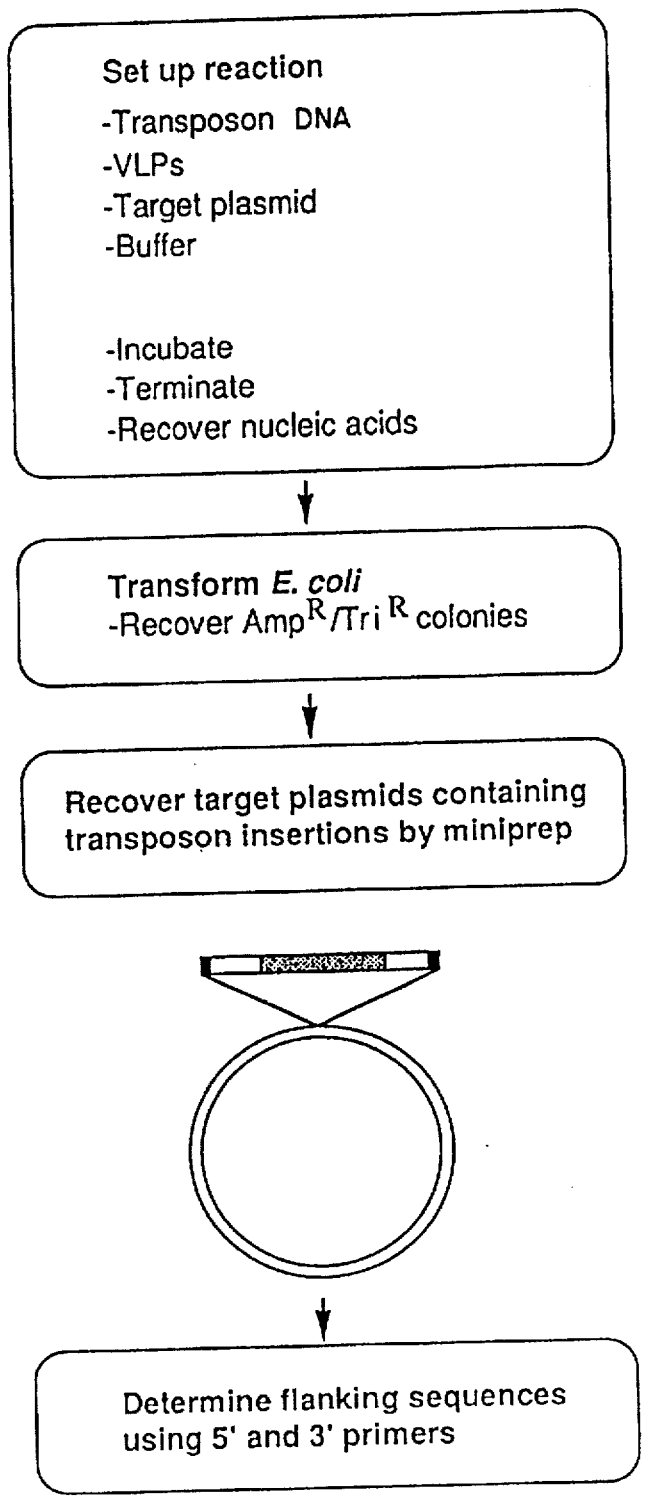
FIG. 1
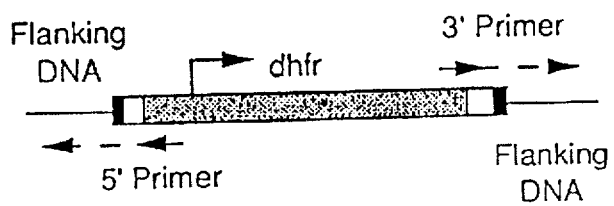

pWAFp

FIG. 8A

```
  1 TCGCGCGTTT CGGTGATGAC GGTGAAAACC TCTGACACAT GCAGCTCCCG GAGACGGTCA   60
 61 CAGCTTGTCT GTAAGCGGAT GCCGGGAGCA GACAAGCCCG TCAGGGGCGG TCAGCGGGTG  120
121 TTGGCGGGTG TCGGGGCTGG CTTAACTATG CGGCATCAGA GCAGATTGTA CTGAGAGTGC  180
181 ACCATACCAC AGCTTTTCAA TTCAATTCAT CATTTTTTT TTATTCTTTT TTTTGATTTC   240
241 GGTTTCTTTG AAATTTTTT GATTCGGTAA TCTCCGAACA GAAGGAAGAA CGAAGGAAGG   300
301 AGCACAGACT TAGATTGGTA TATATATCCA TGAAGAAACA TGAAATTGCC TGAAATTGCC   360
361 CAGTATTCTT AACCCAACTG CACAGAACAA AAACCTGCAG GAAACGAAGA TAAATCATGT   420
421 CGAAAGCTAC ATATAAGGAA CGTGCTGCTA CTCATCCTAG TCCTGTTGCT GCCAAGCTAT   480
481 TTAATATCAT GCACGAAAAG CAAACAAACT TGTGTCTTC ATTGGATGTT CGTACCACCA   540
541 AGAATTACTT GGAGTTAGTT GAAGCATTAG GTCCCAAAAT TTGTTTACTA AAAACACATG   600
601 TGGATATCTT GACTGATTTT TCCATGGAGG GCACAGTTAA GCCGCTAAAG GCATTATCCG   660
661 CCAAGTACAA TTTTTTACTC TTCGAAGACA GAAAATTTGC TGACATTGGT AATACAGTCA   720
721 AATTGCAGTA CTCTGCGGGT GTATACAGAA TAGCAGAATG GCGAGACATT ACGAATGCAC   780
781 ACGGTGTGGT GGGCCTTTTG ATTGTTAGCG GTTGAAGCA GCGGGCAGAA GAAGTAACAA   840
841 AGGAACCTAG TAAGGGTACT ATGTTGACATT G CAAGGCTCC CTATCTACTG             900
901 GAGAATATAC AAGAGACATG GTTGACATTG CAAGAGCGA CAAAGATTTT GTTATCGGCT   960
961 TTATTGCTCA AGAGACGCG GGTGAAGAAG CGATTGGTTG ACAGTATACC ACCGTGATG   1020
1021 CCGTGTGGG TTTAGATGAC AAGGGAGACG CATTGGGTCA ACAGTATAGA ACCGTGATG   1080
1081 ATGTGGTCTC TACAGGATCT GACATTATTA TTGTTGGAAG AGGACTATTT GCAAAGGGAA  1140
1141 GGGATGCTAA GGTAGAGGGT GAACGTACA GAAAAGCAGG CTGGAAGCA TATTTGAGAA   1200
1201 GATGCGGCCA GCAAAACTAA AAAACTGTAT TATAAGTAAA TGCATGTATA CTAAACTCAC  1260
1261 AAATTAGAGC TTCAATTAA TTATATCAGT TATACCCTA TGCGGTGTGA AATACCGCAC   1320
1321 AGATAGCGTAA GGAGAAAATA CCCCATCAGG AAATTGTAAA CGTTAATCCA TGGTTAAAT   1380
1381 TCGCGTTAAA TTTTTGTTAA ATCAGCTCAT TTTTTAACCA ATAGGCCGAA ATCGGCAAAA  1440
1441 TCCCTTATAA ATCAAAAGAA TAGACCGAGA TAGGGTTGAG TGTTGTTCCA GTTTGGAACA  1500
1501 AGAGTCCACT ATTAAAGAAC GTGGACTCCA ACGTCAAAGG GCGAAAAACC GTCTATCAGG   1560
1561 GCGATGGCCC ACTACGTGAA CCATCACCCT AATCAAGTTT TTTGGGGTCG AGGTGCCGTA  1620
1621 AAGCACTAAA TCGGAACCCT AAAGGGAGCC CCCGATTTAG AGCTTGACGG GGAAAGCCGG  1680
1681 CGAACGTGGC GAGAAAGGAA GGGAAGAAAG CGAAAGGAGC GGGCGCTAGG GCGCTGGCAA  1740
1741 GTGTAGCGGT CACGCTGCGC GTAACCACCA CACCCGCCGC GCTTAATGCG CCGCTACAGG  1800
```

FIG. 8B

```
1801 GCGCGTCGCG CCATTCGCCA TTCAGGCTGC GCAACTGTTG GGAAGGGCGA TCGGTGCGGG 1860
1861 CCTCTTCGCT ATTACGCCAG CTGGCGAAAG GGGGATGTGC TGCAAGGCGA TTAAGTTGGG 1920
1921 TAACGCCAGG GTTTTCCCAG TCACGACGTT GTAAAACGAC GGCCAGTGAA TTGTAATACG 1980
1981 ACTCACTATA GGGCGAATTG GAGCTCGAAC ATGTTCACCG CGGTGGCGGC CGCTCTAGAA 2040
2041 CTAGTGGATC CCCGGGCTG CAGGAATTCG ATATCAAGCT TATCGATACC GTCGACCTCG 2100
2101 AGAACATGTT CGGTACCAGC TTTTGTTCCC TTTAGTGAGG GTTAATTCCG AGCTTGGCGT 2160
2161 AATCATGGTC ATAGCTGTTT CCTGTGTGAA ATTGTTATCC GCTCACAATT CCACACAACA 2220
2221 TACGAGCCGG AAGCATAAAG TGTAAAGCCT GGGGTGCCTA ATGAGTGAGG TAACTCACAT 2280
2281 TAATTGCGTT GCGCTCACTG CCCGCTTTCC AGTCGGGAAA CCTGTCGTGC CAGCTGCATT 2340
2341 AATGAATCGG CCAACGCGCG GGGAGAGGCG GTTTGCGTAT TGGGCGCTCT TCCGCTTCCT 2400
2401 CGCTCACTGA CTCGCTGCGC TCGGTCGTTC GGCTGCGGCG AGCGGTATCA GCTCACTCAA 2460
2461 AGGCGGTAAT ACGGTTATCC ACAGAATCAG GGGATAACGC AGGAAAGAAC ATGTGAGCAA 2520
2521 AAGGCCAGCA AAAGGCCAGG AACCGTAAAA AGGCCGCGTT GCTGGCGTTT TTCCATAGGC 2580
2581 TCCGCCCCCC TGACGAGCAT CACAAAAATC GACGCTCAAG TCAGAGGTGG CGAAACCCGA 2640
2641 CAGGACTATA AAGATACCAG GCGTTTCCCC CTGGAAGCTC CCTCGTGCGC TCTCCTGTTC 2700
2701 CGACCCTGCC GCTTACCGGA TACCTGTCCG CCTTTCTCCC TTCGGGAAGC GTGGCGCTTT 2760
2761 CTCATAGCTC ACGCTGTAGG TATCTCAGTT CGGTGTAGT CGTTCGCTCC AAGCTGGGCT 2820
2821 GTGTGCACGA ACCCCCCGTT CAGCCCGACC GCTGCGCCTT ATCCGGTAAC TATCGTCTTG 2880
2881 AGTCCAACCC GGTAAGACAC GACTTATCGC CACTGGCAGC AGCCACTGGT AACAGGATTA 2940
2941 GCAGAGCGAG GTATGTAGGC GGTGCTACAG AGTTCTTGAA GTGGTGGCCT AACTACGGCT 3000
3001 ACACTAGAAG GACAGTATTT GGTATCTGCG CTCTGCTGAA GCCAGTTACC TTCGGAAAAA 3060
3061 GAGTTGGTAG CTCTTGATCC GGCAAACAAA CCACCGCTGG TAGCGGTGGT TTTTTTGTTT 3120
3121 GCAAGCAGCA GATTACGCGC AGAAAAAAAG GATCTCAAGA AGATCCTTTG ATCTTTTCTA 3180
3181 CGGGGTCTGA CGCTCAGTGG AACGAAAACT CACGTTAAGG GATTTTGGTC ATGAGATTAT 3240
3241 CAAAAAGGAT CTTCACCTAG ATCCTTTTAA ATTAAAAATG AAGTTTTAAA TCAATCTAAA 3300
3301 GTATATATGA GTAAACTTGG TCTGACAGTT ACCAATGCTT AATCAGTGAG GCACCTATCT 3360
3361 CAGCGATCTG TCTATTTCGT TCATCCATAG TTGCCTGACT CCCCGTCGTG TAGATAACTA 3420
3421 CGATACGGGA GGGCTTACCA TCTGGCCCCA GTGCTGCAAT GATACCGCGA GACCCACGCT 3480
3481 TTATCAGGGT TATTGTCTCA TGAGCGGATA CATATTTGAA TGTATTTAGA AAAATAAACA 3540
3541 AATAGGGGTT CCGCGCACAT TTCCCCGAAA AGTGCCACCT GGGTCCTTTT CATCACGTGC 3600
3601 TATAAAAATA ATTATAATTT AAATTTTTTA ATATAAATAT ATAAATTAAA AATAGAAAGT 3660
```

FIG. 8C

```
      1          10         20         30         40         50         60
      |          |          |          |          |          |          |
3661  AAAAAAGAA  ATTAAAGAAA AAATAGTTTT TGTTTTCCGA AGATGTAAAA GACTCTAGGG  3720
3721  GGATCGCCAA CAAATACTAC CTTTTATCTT GCTCTTCCTG CTCTCAGGTA TTAATGCCGA  3780
3781  ATTGTTTCAT CTTGTCTGTG TAGAAGACCA CACACGAAAA TCCTGTGATT TTACATTTTA  3840
3841  CTTATCGTTA ATCGAATGTA TATCTATTTA ATCTGCTTTT CTTGTCTAAT AAATATATAT  3900
3901  GTAAAGTACG CTTTTGTTG  AAATTTTTA  AACCTTTGTT TATTTTTTT  TCTTCATTCC  3960
3961  GTAACTCTTC TACCTTCTTT ATTACTTTC  TAAAATCCAA ATACAAAACA TAAAATAAA   4020
4021  TAAACACAGA GTAAATTCCC AAATTATTCC ATCATTAAAA GATACGAGGC GGGTGTAAGT  4080
4081  TACAGGCAAG CGATCCGTCC TAAGAAACCA TTATTATCAT GACATTAACC TATAAAAATA  4140
4141  GGGCTATCAC GAGGCCCCTT CGTC                                         4164
```

FIG. 9A

```
   1 TCGCGCGTTT CGGTGATGAC GGTGAAAACC TCTGACACAT GCAGCTCCCG GAGACGGTCA   60
  61 CAGCTTGTCT GTAAGCGGAT GCCGGGAGCA GACAAGCCCG TCAGGGGCGC TCAGCGGGTG  120
 121 TTGGCGGGTG TCGGGGCTGG CTTAACTATG CGGCATCAGA GCAGATTGTA CTGAGAGTGC  180
 181 ACCATACCAC AGCTTTTCAA TTCAATCAT CATTTTTTT TTATTCTTT TTTGATTC  240
 241 GGTTCTTTG AAATTTTTT GATTCGGTAA TCTCCGAACA GAAGGAAGAA CGAAGGAAGG  300
 301 AGCACAGACT TAGATTGGTA TATATACCGA TATGTAGTGT TGAAGAAACA TGAAATTGCC  360
 361 CAGTATTCTT AACCCAACTG CACAGAACAA AAACCTGCAG GAAACGAAGA TAAATCATGT  420
 421 CGAAAGCTAC ATATAAGGAA CGTGCTGCTA CTCATCCTAG TCCTGTTGCT GCCAAGCTAT  480
 481 TTAATATCAT GCACGAAAAG CAAACAAACT TGTGTGCTTC ATTGGATGTT CGTACCACCA  540
 541 AGGAATTACT GGAGTTAGTT GAAGCATTAG GTCCCAAAAT TTGTTTACTA AAACACATG  600
 601 TGGATATCTT GACTGATTTT TCCATGGAGG GCACAGTTAA GCCGCTAAAG GCATTATCCG  660
 661 CCAAGTACAA TTTTTTACTC TTCGAAGACA GAAAATTGC TGACATTGGT AATACAGTCA  720
 721 AATTGCAGTA CTCTGCGGGT GTATACAGAA TAGCAGAATG GGCAGACATT ACGAATGCAC  780
 781 ACGGTGTGGT GGGCCCAGGT ATTGTTAGCG GTTTGAAGCA GCGGCAGAA GAAGTAACAA  840
 841 AGAACCTAG AGCCCTTTG ATGTTAGCAG AATTGTCATG CAAGGCTCC CTATCTACTG  900
 901 GAGAATATAC TAAGGGTACT GTTGACATTG CGAAGAGCGA CAAAGATTTT GTTATCGGCT  960
 961 TTATTGCTCA AAGAGACATG GGTGAAGAG ATGAAGGTTA CGATTGGTTG ATTATGACAC 1020
1021 CCGGTGTGGG TTTAGATGAC ACAGTATTA CATTGGGTCA ACAGTATAGA ACCGTGGATG 1080
1081 ATGTGGTCTC TACAGGATCT GACATTATTA TTGTTGGAAG AGGACTATTT GCAAAGGGAA 1140
1141 GGGATGCTAA GGTAGAGGGT GAACGTTACA GAAAGCAGG CTGGGAAGCA TATTGAGAA 1200
1201 GATGCGGCCA GCAAAACTAA AAAACTGTAT TGCATGTAAA TGCGGTGTGA CTAACTCAC 1260
1261 AAATTAGAGC TTCAATTTAA TTATATCAGT TATTACCCTA TGCCGTGTGA AATACCGCAC 1320
1321 AGATGCGTAA GGAGAAAATA CCGCATCAGG AAATTGTAAA CGTTAATATT TTGTTAAAT 1380
1381 TCGGTTAAA TTTTTGTTAA ATCAGCTCAT TTTTTAACCA ATAGGCCGAA ATCGGCAAAA 1440
1441 TCCCTTATAA ATCAAAAGAA TAGACCGAGA TAGGGTTGAG TGTTGTTCCA GTTTGGAACA 1500
1501 AGAGTCCACT ATTAAAGAAC GTGGACTCCA ACGTCAAAGG GCGAAAAACC GTCTATCAGG 1560
1561 GCGATGCGCC ACTACGTGAA CCATCACCCT AAATCAAGTT TTTGGGGTCG AGTGCCGTA 1620
1621 AAGCACTAAA TCGGAACCCT AAAGGGAGCC CCCGATTTAG AGCTTGACGG GGAAAGCCGG 1680
1681 CGAACGTGGC GAGAAAGGAA GGGAAGAAAG CGAAAGGAGC GGGCGCTAGG GCGCTGGCAA 1740
1741 GTGTAGCGGT CACGCTGCGC GTAACCACCA CACCCGCCGC GCTTAATGCG CCGCTACAGG 1800
```

FIG. 9B

```
1801 GCGCGTCGCG CCATTCGCCA TTCAGGCTGC GCAACTGTTG GGAAGGGCGA TCGGTGCCGG 1860
1861 CCTCTTCGCT ATTACGCCAG CTGGCGAAAG GGGGATGTGC TGCAAGGCGA TTAAGTTGGG 1920
1921 TAACGCCAGG GTTTTCCCAG TCACGACGTT GTAAAACGAC GGCCAGTGAA TTGTAATACG 1980
1981 ACTCACTATA GGGCGAATTG GAGCTCGAAC ATGTTCACCG CGGTGGGCGC CGCTCTAGAA 2040
2041 CTAGTGGATC CTGCAAGCAG GATAGACGGC ATGCACGATT TGTAATAACA GAGTGTCTTG 2100
2101 TATTTTAAA GAAAGTCTAT TTAATACAAG TGATTATATT AATTAACGGT AAGCATCAGC 2160
2161 GGGTGACAAA ACGAGCATGC TTACTAATAA AATGTTAACC TCTGAGAAG AATTGTGAAA 2220
2221 CTATCACTAA TGTAGCTAT ATCGAAGAAT GGAGTTATCG GAATGCCCC TGATATTCCA 2280
2281 TGGAGTGCCA AAGGTGAACA GCTCCTGTTT AAAGCTATTA CCTATAACCA ATGGCTGTTG 2340
2341 GTTGACGCA AGACTTTTGA ATCAATGGGA GCATTACCCA ACCGAAAGTA TGCGTCGTA 2400
2401 ACAGTTCAA GTTTTACATC TGACAATGAG AACGTATTGA TCTTTCCATC AATTAAAGAT 2460
2461 GCTTTAACCA ACCTAAAGAA AATAACGGAT CATGTCATTG GGCCAGTTT CTACAATAGA 2520
2521 TACAAAAGCC TGATCGATCA AGTAGATACA AGCAATTTA AGGGTTAACA AGTGGCAGCA 2580
2581 GAAGTGATG TTTACTTTCC TGAAATCCCC ATCTGGCAAA AGGGTTAACA AGTGGCAGCA 2640
2641 TTCGCCCTA ACATAAAATTA TAGTTACCAA GCCAAAAGCC GCGCCAGTT TGCGATCCGC 2700
2701 ACGGATTGCC AAACCTGTCA CGCCTTTGT TTCGGTGATC CCTGAGCAGG TGGCGAAAC 2760
2761 TGTGCCAGC GTTAGGCGTC ATATGAAGAT ATCGATACCG TCGACCTCGA GAACATGTTC 2820
2821 ATTGGATGCT GAGAATTCGA TATCAAGCTT GCTTGGCGTA ATCATGGTCA 2880
2881 GGTACCAGCT TTTGTTCCCT TTAGTGAGGG CTCACAATTC CACACAACAT ACGAGCCGGA 2940
2941 TAGCGTGTTC CTGTGTGAAA TTGTTATCCG TGAGTGAGGT AACTCACATT AATTGCGTTG 3000
3001 AGCATAAAGT GTAAAGCCTG GGGTGCCTAA CTGTCGTGCC AGCTGCATTA ATGAATCGGC 3060
3061 CGCTCACTGC CCGCTTTCCA GTCGGGAAAC CTCGTGCGCT CGGTCCTC GCTCACTGAC 3120
3121 CAACGCGCGG GGAGAGGCGG TTTGCGTATT GGGCGCTCTT CCGCTTCCTC GCTCACTGAC 3180
3181 TCGCTGCGCT CGGTCGTTCG GCTGCGGCGA GCGGTATCAG CTCACTCAAA GGCGGTAATA 3240
3241 CGGTTATCCA CAGAATCAGG GGATAACGCA GAAAGAACA TGTGAGCAAA AGGCCAGCAA 3300
3301 AAGGCCAGGA ACCGTAAAAA GGCCGCGTTG CTGGCGTTTT TCCATAGGCT CCGCCCCCCT 3360
3361 GACGAGCATC ACAAAAATCG ACGCTCAAGT CAGAGGTGGC GAAACCCGAC AGACTATAA 3420
3421 AGATACCAGG CGTTTCCCCC TGGAAGCTCC CTCGTGCGCT CTCCTGTTCC GACCCTGCCG 3480
3481 CTTACCGGAT ACCTGTCCGC CTTTCTCCCT TCGGGAAGCG TGGCGCTTTC TCATAGCTCA 3540
3541 CGCTGTAGGT ATCTCAGTTC GGTGTAGGTC GTTCGCTCCA AGCTGGGCTG TGTGCACGAA 3600
```

FIG. 9C

```
3601 CCCCCGTTC AGCCCGACCG CTGCGCCTTA TCCGGTAACT ATCGTCTTGA GTCCAACCCG 3660
3661 GTAAGACACG ACTTATCGCC ACTGGCAGCA GCCACTGGTA ACAGGATTAG CAGAGCGAGG 3720
3721 TATGTAGGCG GTGCTACAGA GTTCTTGAAG TGGTGGCCTA ACTACGCTA CACTAGAAGG 3780
3781 ACAGTATTTG GTATCTGCGC TCTGCTGAAG CCAGTTACCT TCGGAAAAAG AGTTGGTAGC 3840
3841 TCTTGATCCG GCAAACAAAC CACCGCTGGT AGCGGTGGTT TTTTTGTTTG CAAGCAGCAG 3900
3901 ATTACGCGCA GAAAAAAAGG ATCTCAAGAA GATCCTTTGA TCTTTTCTAC GGGGTCTGAC 3960
3961 GCTCAGTGGA ACGAAAACTC ACGTTAAGG ATTTTGGTCA TGAGATTATC AAAAAGGATC 4020
4021 TTCACCTAGA TCCTTTTAAA TTAAAAATGA AGTTTTAAAT CAATCTAAAG TATATATGAG 4080
4081 TAAACTTGGT CTGACAGTTA CCAATGCTTA ATCAGTGAGG CACCTATCTC AGCGATCTGT 4140
4141 CTATTTCGTT CATCCATAGT TGCCTGACTC CCCGTCGTGT AGATAACTAC GATACGGGAG 4200
4201 GGCTTACCAT CTGGCCCCAG TGCTGCAATG ATACCGCGATTA TTGAAGCATT TATCAGGGTT 4260
4261 ATTGTCTCAT GAGCGGATAC ATATTTGAAT GTATTAGAA AATAAACAA ATAGGGGTTC 4320
4321 CGCGCACATT TCCCCGAAAA GTGCCACCTG GGTCCTTTTC ATCACGTGCT ATAAAAATAA 4380
4381 TTATAATTA AATTTTTAA TATAAATATA TAAATTAAAA ATAGAAAGTA AAAAAGAAA 4440
4441 TTAAAGAAAA AATAGTTTTT GTTTTCCGAA GATGTAAAAG ACTCTAGGGG GATCGCCAAC 4500
4501 AATACTACC TTTATCTTG CTCTTCCTGC TCTCAGGTAT TAATGCCGAA TTGTTTCATC 4560
4561 TTGTCTGTGT AGAAGACCAC ACACGAAAT CCTGTGATTT TACATTTTAC TTATCGTTAA 4620
4621 TCGAATGTAT ATCTATTTAA TCTGCTTTTC TTGTCTAATA AATATATATG TAAAGTACGC 4680
4681 TTTTGTTGA AATTTTTAA ACCTTTGTTT ATTTTTTTTT CTTCATTCCG TAACTCTTCT 4740
4741 ACCTTCTTTA TTTACTTTCT AAAATCCAAA TACAAAACAT AAAATAAAT AAACACAGAG 4800
4801 TAATTCCCA AATTATTCCA TCATTAAAAG ATACGAGCCG CGTGTAAGTT ACAGGCAAGC 4860
4861 GATCCGTCCT AAGAAACCAT TATTATCATG ACATTAACCT ATAAAAATAG GCGTATCACG 4920
4921 AGGCCCTTTC GTC                                                   4933
           |         |         |         |         |         |
           10        20        30        40        50        60
```

FIG. 10

```
           10         20         30         40         50         60
  1 TGTTCACCGC GGTGGCGGCC GCTCTAGAAC TAGTGGATCC TGCAAGCAGG ATAGACGGCA  60
 61 TGCACGATTT GTAATAACAG AGTGTCTGT ATTTTTAAAG AAAGTCTATT TAATACAAGT  120
121 GATTATATTA ATTAACGGTA AGCATCAGCG GGTGACAAAA CGAGCATGCT TACTAATAAA  180
181 ATGTTAACCT CTGAGGAAGA ATTGTGAAAC TATCACTAAT GGTAGCTATA TCGAAGAATG  240
241 GAGTTATCGG GAATGGCCCT GATATTCCAT GGAGTGCCAA AGGTGAACAG CTCCTGTTTA  300
301 AAGCTATTAC CTATAACCAA TGGCTGTGG TTGGACGCAA GACTTTTGAA TCAATGGAG  360
361 CATTACCCAA CCGAAAGTAT GCGGTCGTAA CACGTTCAAG TTTTACATCT GACAATGAGA  420
421 ACGTATTGAT CTTTCCATCA ATTAAAGATG CTTTAACCAA CCTAAAGAAA ATAACGGATC  480
481 ATGTCATTGT TTCAGGTGGT GGGAGATAT ACAAAAGCCT GATCGATCAA GTAGATACAC  540
541 TACATATATC TACAATAGAC ATCGAGCCGG AAGGTGATGT TTACTTTCCT GAAATCCCCA  600
601 GCAATTTTAG GCCAGTTTTT ACCCAAGACT TCGCCCTCTAA CATAAATTAT AGTTACCAAA  660
661 TCTGGCAAAA GGGTTAACAA GTGCCAGCAA CGGATTCGCA AACCTGTCAC GCCTTTTGTG  720
721 CCAAAAGCCG CGCCAGGTTT GGATCCGCT GTGCCAGGTCA TTAGGGTCA TATGAAGATT  780
781 TCGGTGATCC CTGAGCAGGT GGCGGAAACA TTGGATGCTG AGAATTCGAT ATCAAGCTTA  840
841 TCGATACCGT CGACCTCGAG AACA                                         864
           10         20         30         40         50         60
```

TO FIG. 11C
→ 2S950126 07.SEQ
→ 2S941115 04.SEQ
← 2S941115 05.SEQ
← 2S950126 08.SEQ
FROM ← 1S950111 10.SEQ
FIG. → 2S941107 18.SEQ
11A → 2S941117 35.SEQ
← 2S941115 03.SEQ

DIAGRAM KEY:
BUMPS LOCATE MOTIFS
MULTIPLE FRAGMENTS SAME STRAND
BOTH STRANDS SEQUENCED
SINGLE FRAGMENT
UNSUBSTANTIATED
START CODON FRAME 1
STOP CODON FRAME 2

FROM FIG. 11A 8.063

IN VITRO TRANSPOSITION OF ARTIFICIAL TRANSPOSONS FOR DNA SEQUENCING

This application is a continuation-in-part of U.S. Ser. No. 08/204,675 filed in the U.S. Patent and Trademark Office on Mar. 2, 1994.

The U.S. Government has a paid-up license in this invention and the right in limited circumstances to require the patent owner to license others on reasonable terms as provided for by the terms of grant number GM36481 and NSF RCD9154644.

BACKGROUND OF THE INVENTION

DNA sequencing has helped revolutionize the way that genes and genomes are studied, and has led to a greater understanding of most aspects of biology. Nevertheless, with efforts underway to map and sequence the genomes of a variety of organisms, the need to improve the efficiency of DNA sequencing has never been greater (1). One of the major problems associated with sequencing large segments of DNA is obtaining sequence information beyond the limits of a single primer extension event. Several techniques are currently used to acquire sequences within the interior of a DNA insert; these include: i) the synthesis of custom primers to "walk" along a segment of DNA (2, 3), ii) shotgun subcloning, which requires a high degree of redundancy for complete sequence recovery (4), or iii) the construction of overlapping exonuclease deletion clones (3, 5). Each of these methods is time-consuming, idiosyncratic and therefore difficult to automate, and/or costly.

Alternatively, transposable elements have been adapted for DNA mapping and sequencing. Examples include: γδ (6), Tn5 (7), Tn10 (8), as well as derivatives of these and other transposons. Although these approaches generally offer great promise, the insertion step is performed in vivo in *E. coli*; hence, transposition may occur into either the plasmid target or the *E. coli* genome, complicating the recovery of target insertions. An additional difficulty arises from host effects on insertion randomness, i.e., "hotspots" and "coldspots" of integration are often observed in vivo (9).

The complete DNA integration reaction employed by certain retroviruses and retrotransposons as part of their normal life cycles can be carried out completely in vitro (10-14) offering a possible alternative to in vivo transposon insertion techniques for DNA sequencing.

There is a need in the art for a simple, reliable technique for generating sets of DNA templates for sequencing any target. In particular there is a need for sets of DNA templates which are amenable to automated sequencing with a single set of primers.

SUMMARY OF THE INVENTION

It is an object of the invention to provide methods for providing templates for DNA sequencing.

It is another object of the invention to provide methods for sequencing such DNA templates.

It is yet another object of the invention to provide a kit for DNA sequencing.

It is yet another object of the invention to provide an artificial transposon.

It is still another object of the invention to provide plasmids for preparing artificial transposons.

It is yet another object of the invention to provide methods for the generation in vitro of insertions into a target DNA molecule.

These and other objects of the invention are provided by one or more of the embodiments of the invention described below. In one embodiment a method is provided for preparing templates for DNA sequencing. The method comprises the steps of:

incubating in vitro: (1) a population of a target DNA, said target DNA comprising a region of DNA to be sequenced, (2) a retroviral or retrotransposon integrase, and (3) an artificial transposon having two termini which are substrates for said integrase, wherein the molar ratio of artificial transposon to target DNA is at least 1:1, to form a population of target DNAs with quasi-randomly integrated insertions of the artificial transposon;

transforming host cells with the population of target DNAs with quasi-randomly integrated insertions of the artificial transposon;

selecting those host cells which have been transformed with a target DNA with an insertion of the artificial transposon;

isolating target DNA with an insertion of the artificial transposon from those host cells which have been transformed with a target DNA with an insertion of the artificial transposon, said target DNA with an insertion of the artificial transposon being suitable for use as a DNA sequencing template.

In another embodiment a method is provided for sequencing DNA. The method comprises the steps of:

incubating in vitro (1) a population of a target DNA, said target DNA comprising a region of DNA to be sequenced, (2) a retrovirus or retrotransposon integrase, and (3) an artificial transposon having two termini which are substrates for said integrase, wherein the molar ratio of artificial transposon to target DNA is at least 1:1, to form a population of target DNAs with quasi-randomly integrated insertions of the artificial transposon;

transforming host cells with the population of target DNAs with quasi-randomly integrated insertions of the artificial transposon;

selecting those host cells which have been transformed with a target DNA with an insertion of the artificial transposon;

isolating target DNA with an insertion of the artificial transposon from those host cells which have been transformed with a target DNA with an insertion of the artificial transposon, said target DNA with an insertion of the artificial transposon being suitable for use as a DNA sequencing template;

hybridizing to said isolated target DNA with an insertion of the artificial transposon a primer which is complementary to a terminus of the artificial transposon;

extending said primer to determine a nucleotide sequence of DNA flanking said artificial transposon in said isolated target DNA with an insertion of the artificial transposon.

In still another embodiment of the invention a method for sequencing DNA is provided. The method comprises the steps of:

providing a population of target DNAs with quasi-randomly integrated insertions of an artificial transposon, said artificial transposon having termini which are substrates for a retrovirus or a retrotransposon, said population of target DNAs having been formed by in vitro insertion of said artificial transposon into the target DNAs using a retroviral or retrotransposon integrase and a molar ratio of artificial transposon to target DNA of at least 1:1;

hybridizing to individual target DNAs of said population a primer which is complementary to a terminus of the artificial transposon;

extending said primer to determine a nucleotide sequence of target DNA flanking said artificial transposon.

In still another embodiment of the invention a kit for DNA sequencing is provided. The kit comprises:

an artificial transposon having termini which are substrates for a retroviral or retrotransposon integrase;

a retroviral or retrotransposon integrase;

a buffer for in vitro transposition of said artificial transposon, said buffer having a pH of 6 to 8 and 1 to 50 mM of a divalent cation; and a primer which is complementary to a terminus of said artificial transposon.

In an additional embodiment of the invention an artificial transposon is provided. The transposon consists of a linear DNA molecule comprising:

a marker gene;

a sequence of yeast retrotransposon Ty1, said sequence selected from the group consisting of a U5 sequence and a U3 sequence, said sequence flanking said marker gene on its upstream end, said sequence consisting of 4 to 11 bp of terminal sequences of said Ty1; and a sequence of yeast retrotransposon Ty1, said sequence selected from the group consisting of a U5 sequence and a U3 sequence, said sequence flanking said marker gene on its downstream end, said sequence consisting of 4 to 11 bp of terminal sequences of said Ty1.

In yet an additional embodiment of the invention a DNA molecule useful for generating artificial transposons is provided. The DNA molecule comprises:

an origin of replication;

a first selectable marker DNA;

two blunt-ended transposon termini of at least 4 bp each, said termini being substrates for yeast retrotransposon Ty1 integrase, said transposon termini flanking a first restriction enzyme site useful for insertion of a second selectable marker gene to form an artificial transposon;

a second restriction enzyme site flanking said two transposon termini, wherein digestion with said second restriction enzyme liberates a blunt-ended fragment having said transposon termini at either end of the fragment, the fragment thereby liberated being an artificial transposon.

In still another embodiment of the invention a method for in vitro generation of insertions into a target DNA is provided. The method comprises the steps of:

incubating in vitro (1) a population of a target DNA, (2) a retroviral or retrotransposon integrase, and (3) an artificial transposon having termini which are substrates for said integrase, wherein the molar ratio of artificial transposon to target DNA is at least 1:1, to form a population of target DNAs with quasi-randomly integrated insertions of the artificial transposon;

transforming a host cell with the population of target DNAs with quasi-randomly integrated insertions of the artificial transposon;

selecting those host cells which have been transformed with a target DNA with an insertion of the artificial transposon.

The in vitro systems of the present invention offer several advantages over in vivo transposition systems: i) special bacterial strains are not required, ii) potential host effects are avoided, and iii) an in vitro reaction is amenable to biochemical alteration and parameter optimization. Thus a simple and reliable method is provided for generating large amounts of sequence information, such as is required for sequencing of entire genomes of particular organisms.

BRIEF DESCRIPTION OF THE DRAWINGS

FIG. 1. Overview of artificial transposon insertion into plasmid targets.

The basic steps involved in generating artificial transposon insertions in target plasmids are indicated. Note the following: DNA sequences to be determined (dashed line) trimethoprim resistance (tri$^r$) gene (shaded box); target plasmid (double circle); PART (primer island artificial transposon) (box); Ty1 U3 termini (filled rectangles).

Figure 2A:
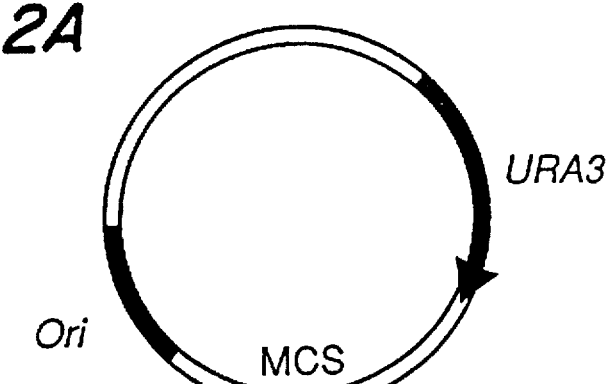
Figure 2B:
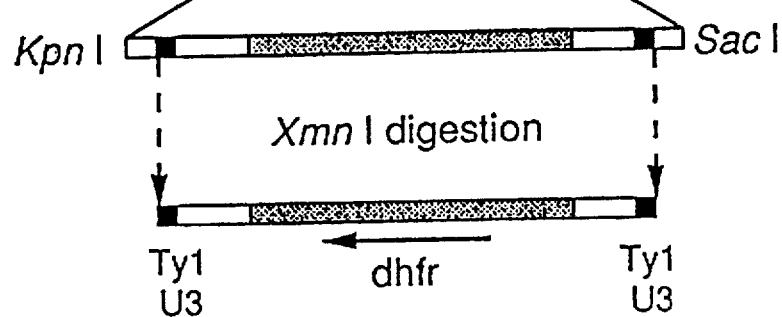

FIGS. 2A–2B. pAT-1 and pAT-2.

Figure 2C:
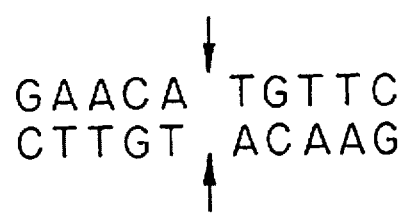

FIG. 2A. The backbone common to pAT-1 and pAT-2 is shown to contain the yeast URA3 gene, a bacterial origin of replication (ori) and a multicloning site (mcs). pAT-2, containing the PART insert, is depicted. FIG. 2B. The PART which is created upon digestion with Xmn I, is shown. It contains the dhfr (dihydrofolate reductase) gene (stippled), the pBLUESCRIPT mcs (white boxes), and Ty1 U3 cassettes (filled rectangles), as well as two unique primer sites for sequencing the DNA flanking an insertion site. FIG. 2C. The sequence at Ty1 U3/Xmn I cassettes. The arrows indicate the Xmn I cleavage site. The shaded areas indicate Ty1 U3 sequences (one on either side of the arrows), while the entire sequence encodes a recognition site for Xmn I.

Figure 3:
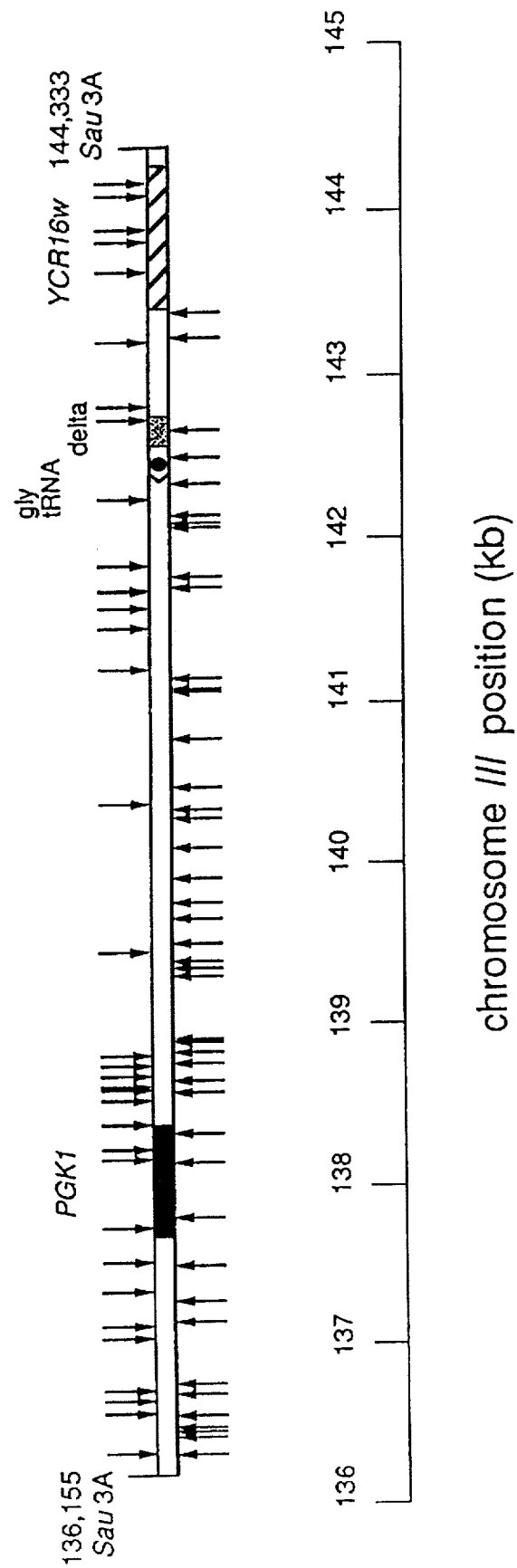

FIG. 3. PART insertions in clone p76-2.

The 8 kb insert of clone p76-2, containing a segment of yeast chromosome III, is shown along with the sites of 78 independent PART insertions (arrows). The orientation of transposon insertion is indicated: (↓) Forward (the dhfr gene in the artificial transposon is transcribed left to right, or (↑) Reverse. This region of chr. III contained on the insert includes the PGK 1 gene (black box), a glycine tRNA gene (black circle with arrowhead indicating direction of transcription), a Ty1 solo delta (stippled box) and the YCR16w locus (striped box). The PART insertion locations were determined by sequencing one or both insertion junctions.

Figure 4:
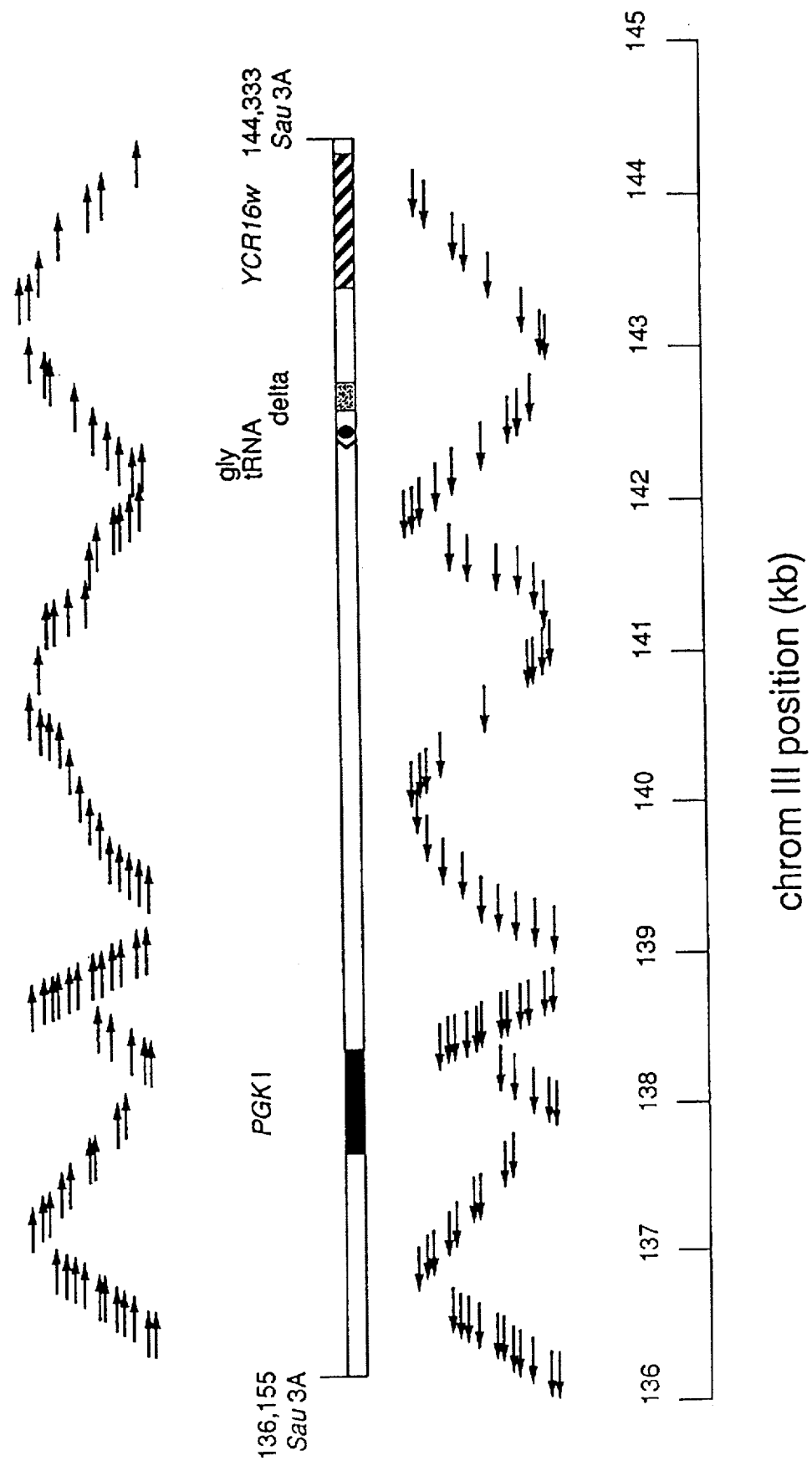

FIG. 4. Conceptual contig map.

The locations of the 78 PART insertions were used to construct a conceptual contig map based on the following assumptions: i) two primer extensions would be initiated from each PART (one in each direction) and ii) each extension would lead to the recovery of 250 bp of useful DNA sequence information.

Figure 5:
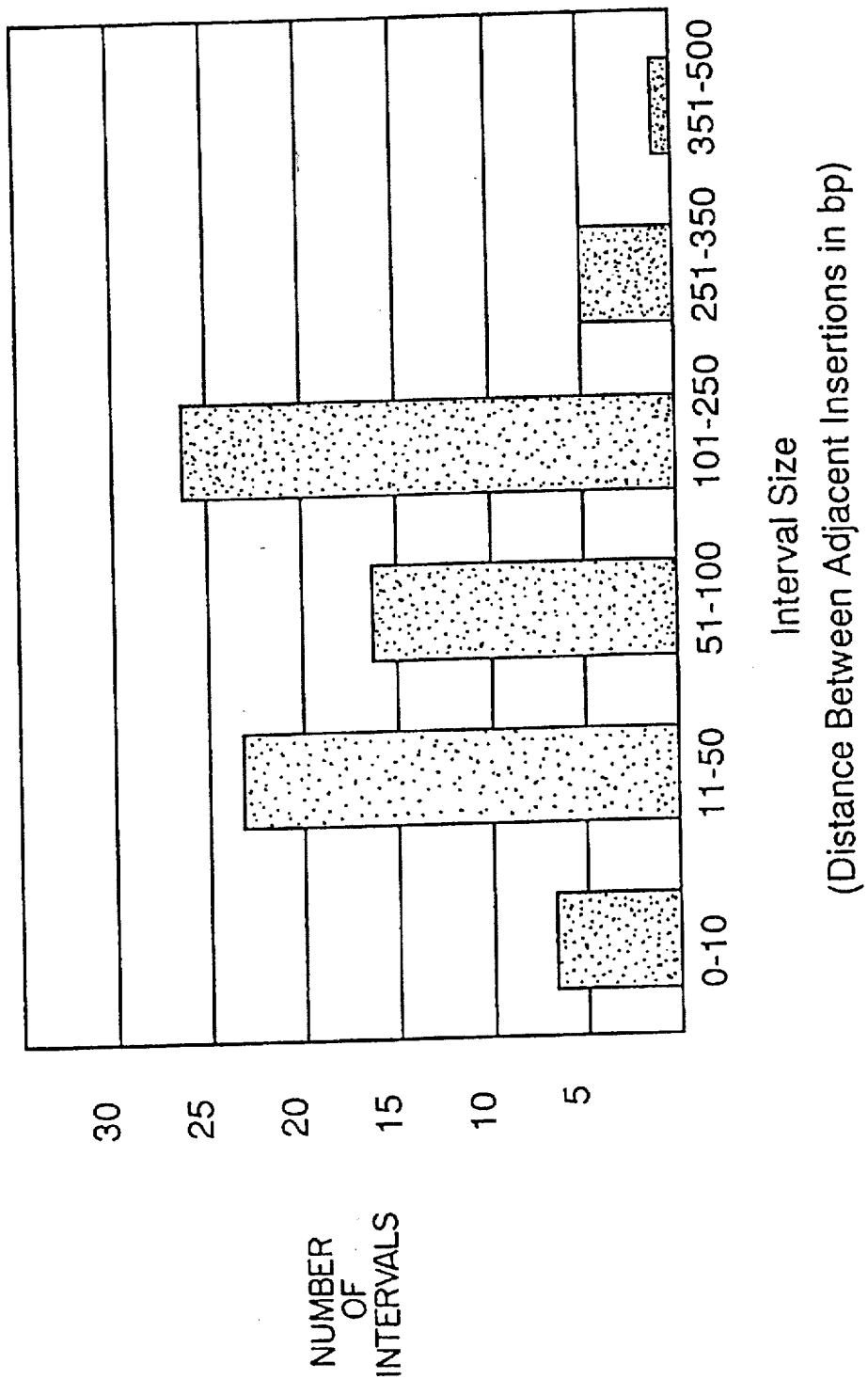

FIG. 5. Interval Sizes of PART insertions into p76-2.

The size of intervals between individual insertions of PART into p76-2 (i.e., the distance between adjacent insertions in bp) were grouped and the number of intervals falling within each group is graphically represented.

Figure 6:
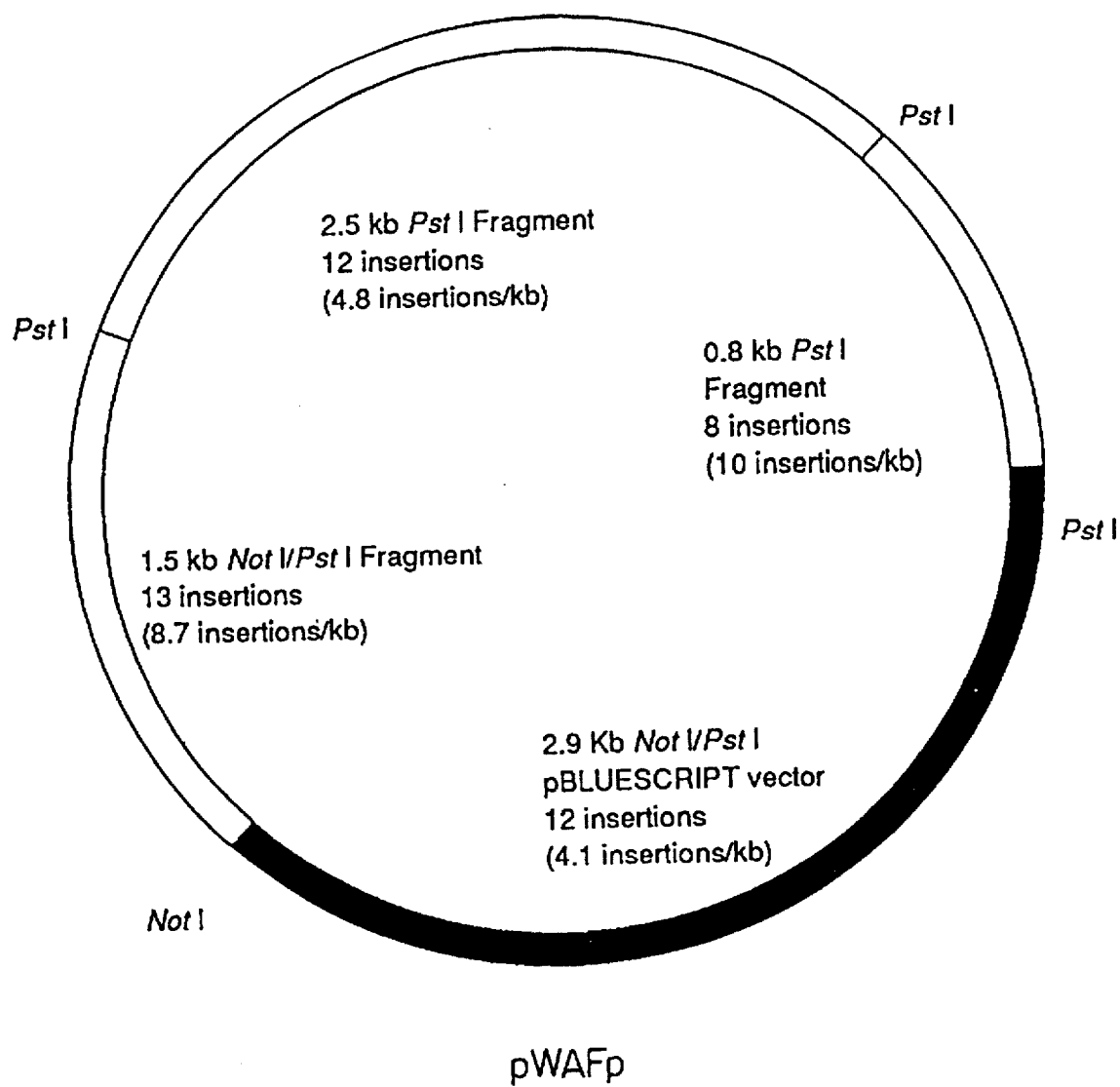

FIG. 6. Distribution of PART insertions in plasmid pWAFp.

Plasmid pWAFp contains a 5 kb insert of human DNA encoding the WAF-1 promoter. We generated PART insertions into this target using an artificial transposon prepared by PCR and digestion with Bbs I to generate U3 and U5 sequences at the upstream and downstream ends of the transposon, respectively. Of 45 insertions analyzed, 12 mapped to the pBLUESCRIPT vector fragment (shown in black), 13 mapped to the 1.5 kb Not I/Pst I fragment of the WAF-1 insert, 12 mapped to the 2.5 kb Pst I fragment of WAF-1 (WAF-1 sequences are solid white). Hence, insertions were recovered from all regions of this target plasmid, and the insertion frequencies ranged from 4.1 insertions/kb to 10 insertions/kb target DNA. This set of insertions was then used to directly recover greater than 90% of the WAF-1 DNA sequence.

Figure 7:
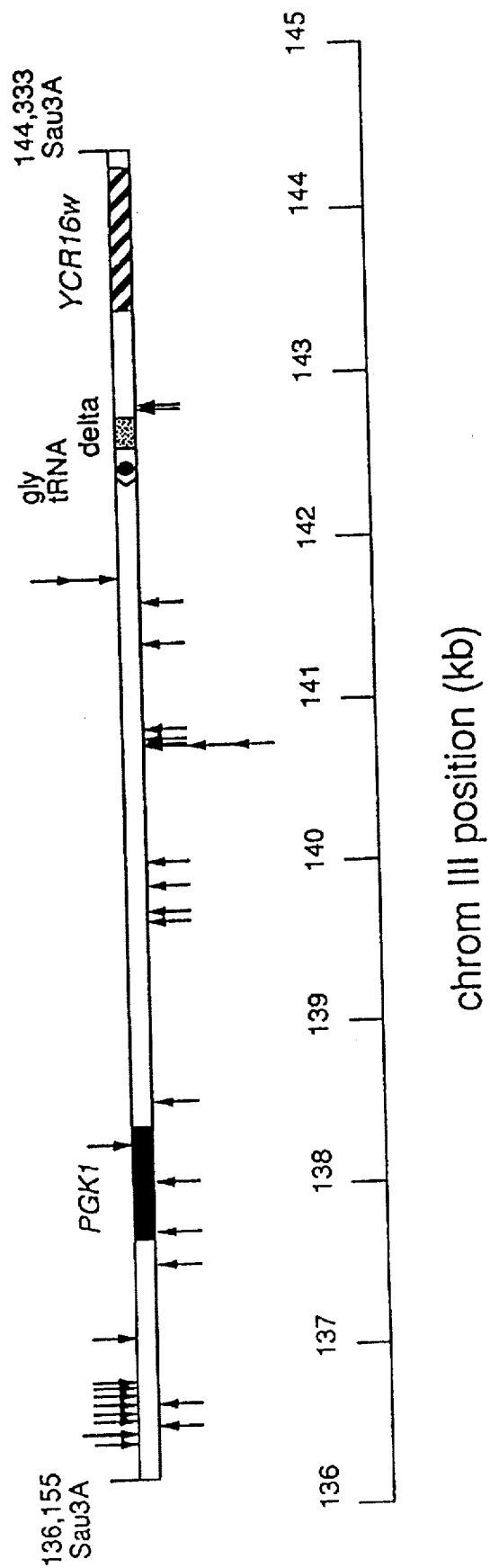

FIG. 7. Distribution of insertions into yeast chromosome III.

An artificial transposon having one U3 and one U5 terminus, each 4 pb in length, was generated by PCR, digested with Bbs I, and filled-in with Klenow fragment of DNA polymerase I. Distribution of insertions are shown on a map of the chromosome III segment of DNA contained on the target plasmid.

FIGS. 8A–8C. The nucleotide sequence of pAT-1.

FIGS. 9A–9C. The nucleotide sequence of pAT-2.

FIG. 10. The nucleotide sequence of the PART from pAT-2.

Figure 11A:
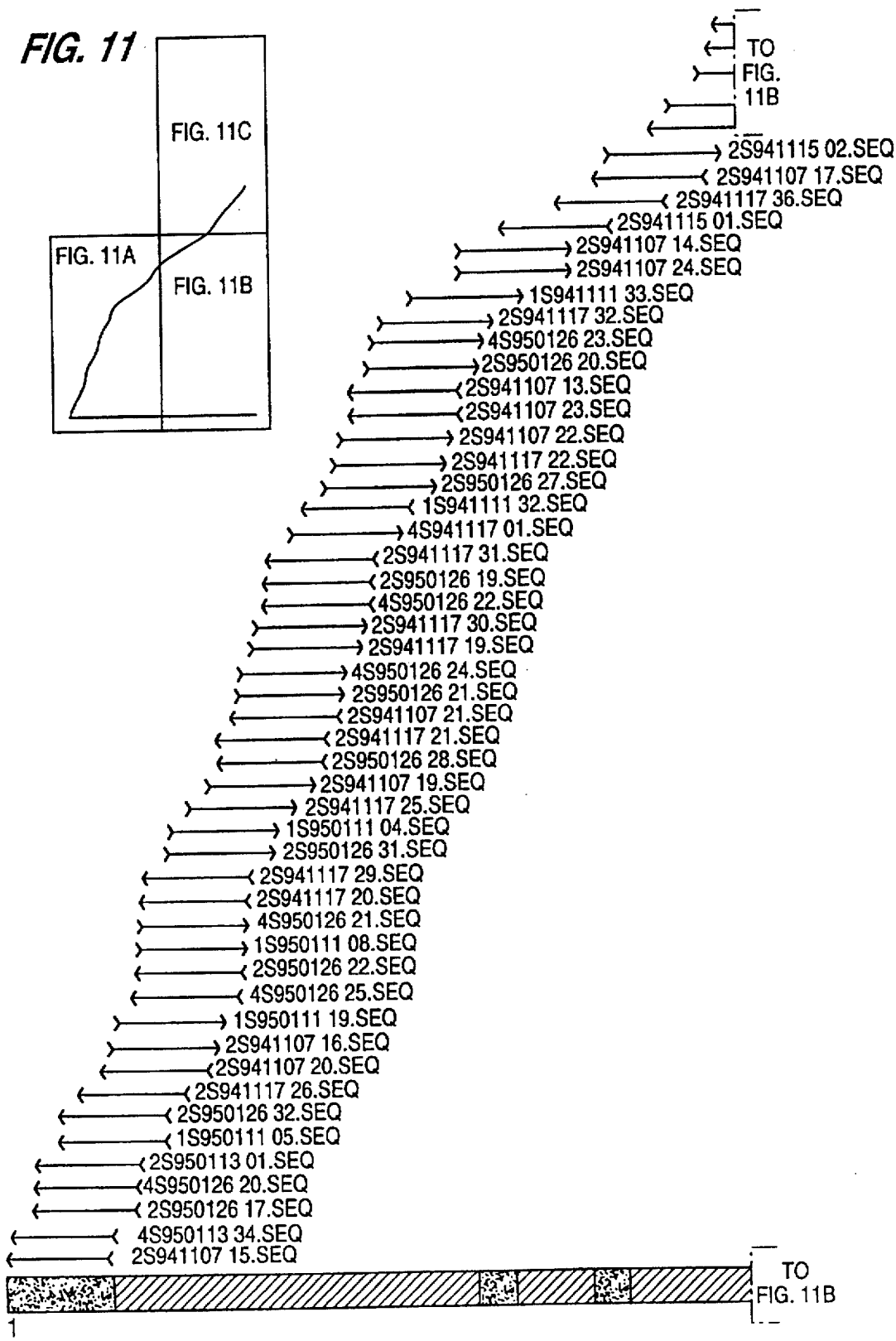
Figure 11B:
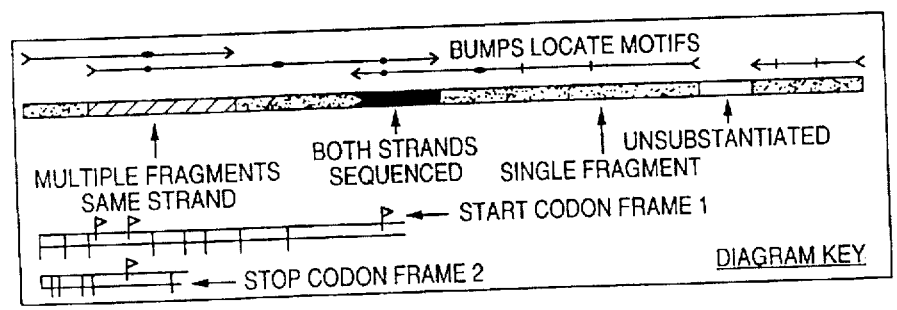
Figure 11C:
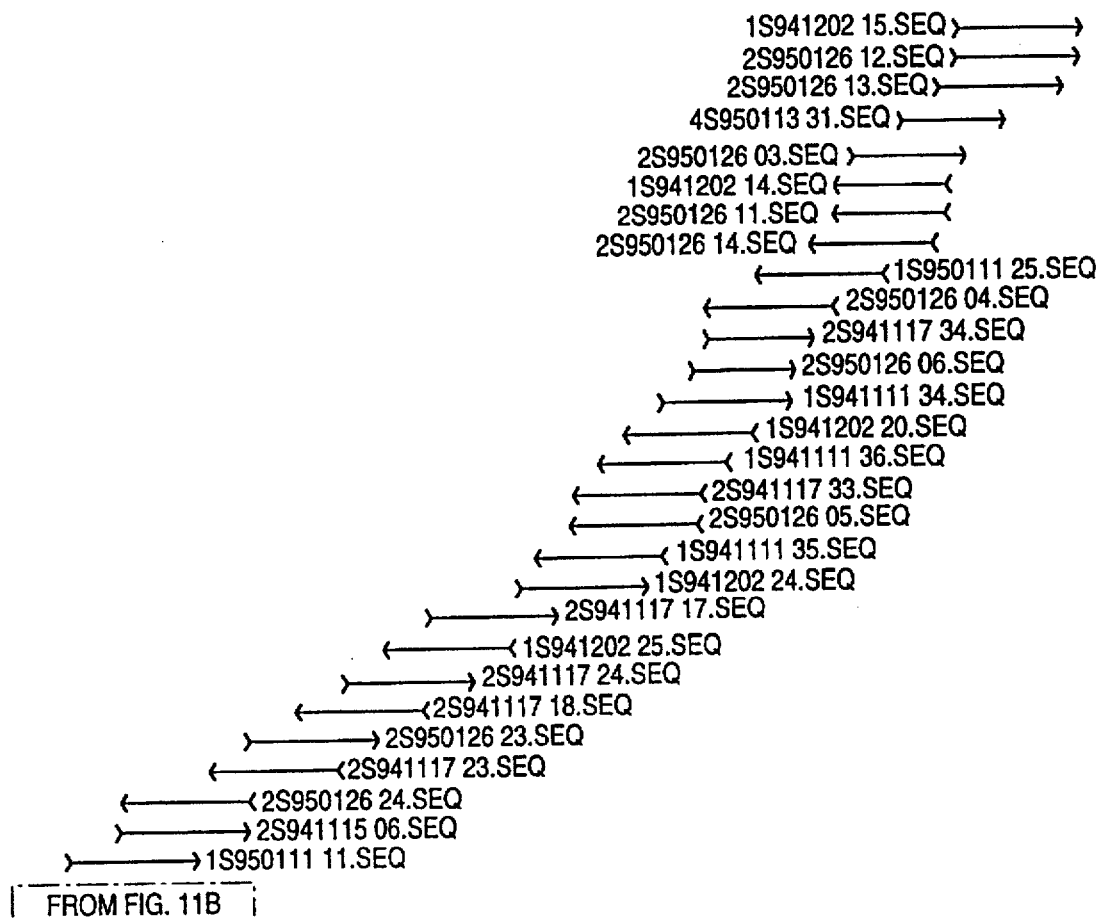

FIGS. 11A–11C. Sequence contig map for 8 kb region of cosmid F13544.

169 independent AT-2 insertions were generated in the cosmid F13544 by in vitro integration. A collection of 43 insertions which were found to map to an 8 kb region by restriction mapping were assembled and sequenced using primers SD118 and 119 in conjunction with ABI Prism technology. A contig map of the sequencing project is indicated. Each arrow represents a single primer extension event. Beneath is a map of sequence completion. Black areas indicate sequence on both strands, whereas hatched areas are on one strand only.

Figure 12:
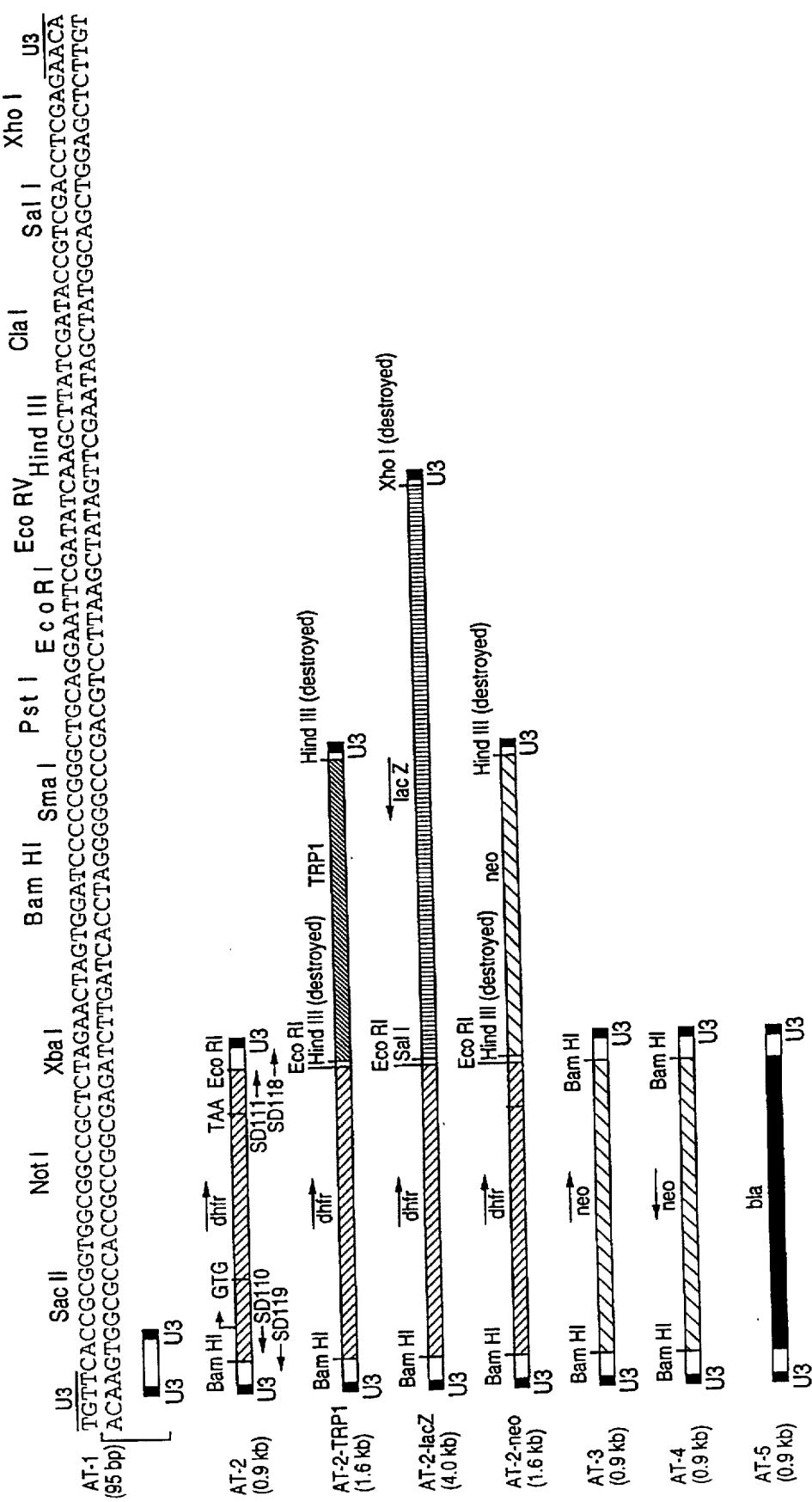

FIG. 12. Artificial transposons.

Eight different artificial transposons, including the AT-1 sequence and structure, are shown. Each was derived from either pAT-1 or pAT-2, and is prepared from its plasmid with the same Xmn I strategy used for these plasmids.

DETAILED DESCRIPTION OF THE PREFERRED EMBODIMENTS

It is a discovery of the present invention that a transposon insertion technique that is carried out entirely in vitro may be applied to a variety of problems, including DNA sequencing. This technique employs artificial transposons which are created using a plasmid construct, and retroviral or retrotransposon integrase, which may be provided in the form of vital or virus-like particles (VLPs), which mediates the insertion of these transposons into target DNA molecules.

We have developed new methods for creating artificial transposons and efficiently inserting these transposons into DNA targets, in vitro. There are three key aspects of the process: i) the in vitro integration reaction is highly efficient, giving rise to thousands of integrations per reaction; with most plasmid targets, this efficiency approaches one insertion per phosphodiester bond. ii) the insertion process is sufficiently random that transposon integrations occur throughout target plasmid sequences, and iii) virtually any DNA sequence or combination of sequences can, in principle, serve as an artificial transposon. These three features combine to make this an extremely versatile method of generating recombinant DNA molecules.

Artificial transposons are ideal for DNA sequencing: i) a large number of transposon insertions can be easily assembled from a single integration reaction, allowing the recovery of insertions suitably spaced to facilitate sequencing of a DNA segment, ii) the transposon can be engineered to contain desired features useful for DNA mapping or sequencing, and iii) since each transposon carries two unique primer sites, the nucleotide sequence flanking each insertion site can be rapidly and efficiently determined. A set of plasmids bearing artificial transposon insertions are especially useful for sequencing because all the plasmids can be sequenced in parallel using a defined pair of primers. This is in contrast to the inefficient "series" approach of primer walking, in which each sequence is used to specify the next primer. Hence, artificial transposons are flexible and extremely efficient for generating DNA sequencing templates useful for both small and large-scale DNA sequencing projects.

There are three macromolecular components to the in vitro integration reaction: i) an artificial transposon, ii) retroviral or retrotransposon integrase and iii) a DNA target. These three components are mixed together in a reaction containing the appropriate buffer and cofactors. In the case of yeast retrotransposon Ty1, the reaction is briefly incubated at 30° and 37° Celsius, and terminated by adding EDTA and heating to 65° Celsius. Finally, the nucleic acids are phenol/chloroform extracted and ethanol precipitated. The recovered DNA is used to transform a host cell to drug resistance (or other suitable selectable marker), allowing the identification of target molecules which have received a transposon integration (FIG. 1). A set of transposon-bearing target DNA molecules may then be used directly to obtain the DNA sequences flanking the insertion sites, using two primers corresponding to the transposon termini; a collection of such insertions can be used for the efficient recovery of DNA sequence information from the region of interest.

We have focused our initial efforts on developing a specific application of this technology, i.e., in vitro insertion of "primer island" artificial transposons (PARTs) into plasmid targets for the purpose of DNA mapping and sequencing. In addition to the features mentioned above (efficiency of integration, randomness of insertion, and flexibility of transposon), this system has other advantages compared with existing methods, including: i) the in vitro protocol is simple and highly reliable, even in the hands of a novice, ii) the PART does not contain large terminal repeats which, in Tn5 and Tn10-based systems, hinder access to sequences flanking the insertion junctions, and iii) the reaction is carded out completely in vitro and therefore is amenable to biochemical alteration and parameter optimization; this may be especially useful with unusual DNA templates such as those containing tandem sequence repeats, high GC content, or unusual template topology which might represent difficult targets.

Importantly, transposon integration within targets was sufficiently random that insertions were recovered from all regions of target DNAs. Hence, Ty1 integrase-mediated integration in vitro is, at a minimum, a nearly-random process. It may, in fact, be totally random. This will only become clear upon testing large numbers of targets containing different DNA sequence features. Nevertheless, our current results strongly support a model of quasi-random insertion with no apparent major biases. In contrast, this feature is not generally observed of other transposon systems adapted for DNA sequencing; instead, hotspots and coldspots of insertion frequently lead to a non-random distribution of insertions rendering these systems incapable of accessing large segments of DNA sequence, or high levels of wasteful redundancy in other regions. These problems have been circumvented in some systems with mutant transposases which display altered target specificity (9). However, this approach provides only a limited relaxation of transposase-specified target specificity. It is known that host cell factors contribute to target specificity in vivo for both Tn10 (9, 9a) and Ty1 (28); such target specificity is eliminated by the use of in vitro systems as taught herein. Fortunately, the process of artificial transposon integration in vitro by retroviral and retrotransposon integrases, such as Ty1 integrase, displays random-like behavior (FIG. 2), making it ideal for the purpose of DNA sequencing. Quasi-random, according to the present invention, means that insertions can be obtained in virtually any sequence at a spacing of at least one integration per kb. In practice, integrations have been obtained at maximum spacings of as low as one integration per 500 bp, or even one integration per 400 bp. In contrast, large cold-spots have been found in targets of Ty1 transposition in vivo.

Because our method of constructing artificial transposons is very versatile, transposons containing a variety of sequences can be constructed for a number of specific applications. For example, other markers can be inserted into the multicloning site (mcs) site of pAT-1, including but not limited to yeast and mammalian drug-selectable or auxotrophic genes, generating marker cassettes that can act as transposons. Such artificial transposons can be used for "marker addition", i.e., the insertion of a useful auxotrophic marker into an acceptable region of a plasmid of interest. For use in bacteria or yeast, for example, pAT-1 derivatives containing a variety of selectable markers in the mcs can be constructed, and the marker of choice (auxotrophic, drug resistance, suppressor, etc.) can be added to a target plasmid with a simple in vitro integration reaction. Indeed, the products of a single integration reaction can be viewed as an "integration library" containing a collection of insertions, each clone containing a single insertion at a particular phosphodiester bond. Should it be necessary, an insertion at any specific phosphodiester bond can be identified with conventional library screening methods, using a junction oligonucleotide as a probe. Hence, using a custom artificial transposon, and applying the appropriate screening method, recombinant molecules of a desired structure can be recovered.

In addition to the artificial transposon, the other two components of the system, i.e., the integrase and the target, are also versatile. For example, other integrases or transposases can effect an equivalent or nearly-equivalent in vitro integration reaction. In addition, mutant integrases are also useful. The specific properties of such integrases might together provide a wider range of integration preferences or frequencies. Also, rather than providing the integrase in the form of vital particles or VLPs, purified integrases can be used. These may display altered levels of activity or stability, relative to VLP-associated integrases.

The in vitro integration reaction can employ a variety of DNA targets. Plasmids, including cosmids, artificial chromosomes, as well as bacteriophage or viral vectors are useful. Bacteriophage lambda DNA has been used as a target in similar reactions using Moloney murine leukemia virus (10) and Ty1 integrases (11,12) provided in the form of viral particles.

The PART-based system for generating DNA sequencing templates can be readily applied to the development of high throughput, massively parallel DNA sequencing strategies. The high degree of randomness of insertion and the large fraction of clones generating useful sequence data mean that a shotgun approach to sequencing of large recombinant plasmids, including cosmids as well as P1 and bacterial artificial chromosomes, is feasible and highly suited to automation. Random doubly drug resistant colonies can be selected, their DNA extracted, and fed directly into an automated sequencing apparatus. All of these steps are amenable to automation. Because a single set of optimized primers can be used to sequence an entire set of plasmid derivatives, all of the steps can be done in parallel without operator intervention with regard to primer design and selection, etc. Hence, although artificial transposon-facilitated DNA sequencing is predicted to be very useful for small-scale sequencing projects, it may be even more useful for massive projects such as the effort underway to map and sequence the human genome.

The artificial transposon which is employed according to the present invention contains a 3'-hydroxyl and is blunt-ended. Such molecules can be prepared using restriction enzymes which make staggered cuts followed by a "filling-in" reaction with a DNA polymerase, such as Klenow fragment of DNA polymerase I. Alternatively, the artificial transposon can be prepared by a PCR. Typically the ends of PCR products require "trimming" to generate blunt ends. Thus a restriction enzyme, such as Xmn I, which makes blunt-ended termini can be used to trim a PCR product. Most simply, an artificial transposon contained in a plasmid can be isolated from the plasmid with a restriction enzyme, such as Xmn I, which makes blunt-ended termini. This provides a homogenous preparation of blunt-ended fragments in one step.

Integrase activity can be provided by virus-like particles, in the case of yeast retrotransposon Ty1, or by cellular nucleoprotein complexes in the case of retroviral particles. Alternatively, purified integrase may be used. It is desirable that the artificial transposon be added to the in vitro transposition incubation mixtures as protein-free DNA preparations. Although some native transposon DNA may be present in the integrase preparations, typically such transposons will not be genetically marked, and will be present in significantly lower molar amounts than the artificial transposon.

DNA contained within a transposon's termini may be any desirable marker or even a cryptic sequence. Antibiotic resistance genes, useful for either prokaryotes or eukaryotes are often useful. Auxotrophic markers are also useful, especially in yeast. Cis-acting regulatory elements, such as promoters, may also be desired to ascertain function of previously unknown regions flanking an insertion. Marker DNAs also includes other non-coding features, such as restriction sites, primer binding (hybridization) sites, etc.

The ratio of artificial transposon to target DNA has been found to be a significant factor in the efficiency of the reaction. Desirably the molar ratio will be at least 1:1, and more preferably the molar ratio will be at least 2.5:1, 10:1 or 50:1.

Host cells may be transformed by any means known in the art, including transfection, transduction, electroporation, etc. Selection of transformed cells is typically and conveniently carded out by a genetic selection means, although genetic and biochemical screening methods may also be employed.

In the case of Ty1 transposition, the use of the entire U3 or U5 terminal sequences has been found to be unnecessary. Thus as little as 4 bp of terminal sequence of U3 and/or U5 can be used. (The sequence of U3 and U5 are disclosed in FIG. 5 of reference 12.) While there is some evidence that other unrelated sequences may he suitable as a substrate for integrase enzymes to generate single transposon-end joining products (14), such sequences may not be suitable for generating the two transposon-end, complete integration product necessary for the present invention.

Primers which are employed for sequencing according to the present invention are those which are known in the art for dideoxy-type sequencing. These are typically synthetic, single-stranded oligonucleotides of about 12–60 bases in length. It is desirable, according to the present invention that the primers for sequencing each flank of the inserted transposon be unique. Therefore, if the two transposon termini are identical, which they can be, the primer complementarity must extend into or be wholly derived from the "marker region" so that each primer only hybridizes to a single end of the transposon. Primers "complementary to a terminus of an artificial transposon" are those oligonucleotides which are 12 to 60 bases in length which are derived from the terminal approximately 150 bp of the artificial transposon. Primer sequences which are optimized for DNA sequencing can easily be designed into the artificial transposon.

Viral particles, according to the present invention are nucleoprotein complexes which are isolated from cellular extracts of infected cells. In the case of yeast retrotransposon Ty1, the particles are known as virus-like particles. An integrase activity can be purified from such particles using protein purification techniques known in the art. While Ty1 is exemplified in this application, it is believed that its closely related yeast retrotransposon Ty2 will be equally useful.

In addition, retroviral and other integrases may also be used according to the present invention. Avian myeloblastosis virus (AMV) integrase can be used to mediate the concerted integration of an artificial transposon into a target DNA (30). Murine leukemia virus (MLV) and human immunodeficiency virus (HIV) retroviral integrases mediate quasi-random insertion of artificial transposons into target DNAs (31). The 3-D structure of HIV-1 integrase core domain has been shown to be similar to the bacterial transposase, MuA (32). Thus bacterial transposases could also be used in a similar manner.

It has been found that divalent cations are necessary for transposition. Suitable concentrations of magnesium or manganese ions range from about 1 to about 50 mM. Preferably the concentration is between about 5 and 45 mM. The pH range which is suitable for in vitro transposition is broad, from pH 6 to 8, and may desirably be from pH 7 to pH 8.

In addition to the application of PART technology to the sequencing of DNA, there are a number of other applications which are possible, owing to the high efficiency and randomness of insertion of PARTs. Some of these are outlined below.

1. DNA sequencing and mapping i) Small-scale DNA sequencing.

Example: A 3.5 kb segment of DNA is cloned into a plasmid cloning vector. The investigators wish to obtain the complete nucleotide sequence of this 3.5 kb insert, on both strands using polymerase-based (Sanger) dideoxy sequencing. PART insertions are generated throughout the plasmid in vitro. The collection is screened by restriction mapping to determine whether individual PART insertions are located in the plasmid backbone or the insert, and a collection of target plasmids bearing insertions every 100–200 bp in the insert is recovered. Each PART is then used to sequence the DNA on both sides of the insertion, using unique primers homologous to the termini of the PART. Since standard dideoxy sequencing protocols lead to the recovery of 200–300 bp (or more) useful sequence information, the entire sequence of the 3.5 kb insert is recovered, on both strands.

ii) Large-scale sequencing.

Example: A yeast artificial chromosome (YAC), bacterial artificial chromosome (BAC), or other vehicle used for the propagation of large segments of DNA contains a large segment of human DNA that requires DNA sequence analysis. Assuming that a 400 kb YAC is used, the YAC is resolved on a pulsed field gel cast with low-melting point agar, and excised. PART insertions are generated in vitro within the YAC. A specialized PART derivative, containing a selectable yeast marker is used to enable the facile recovery of PART insertions by transforming the collection into yeast by protoplast fusion, with subsequent selection for complementation of an auxotrophy. PART insertions are recovered throughout the YAC in this manner. Each PART insertion is then used to recover sequence from the flanking DNA in both directions by cycle sequencing, using a thermostable polymerase. YACs bearing PART insertions are shotgun sequenced until the entire sequence is recovered. The original linkage of the sequence is maintained throughout the procedure, making data assimilation simpler than most large-scale sequencing methods. Finally, many aspects of this process are amenable to automation.

iii) DNA Mapping.

Using PART insertions such as those described above, a PART map could be constructed in a DNA segment of interest. Since the PART contains a number of useful restriction sites (6-bp and 8-bp cutters), the location of the insertions relative to the endpoints of the insert could be determined by cutting the clone with an enzyme such as Not I, and running the products on the appropriate gel. The sizes of the products would yield information about the location of the PART insertion relative to the ends and other sites such as known genes or Not I sites. The sequence information recovered from such a PART insertion could then be correlated with a map position. This approach enables the rapid assignment of a sequence tag to a map position, which would be a useful intermediate on the way to completing the entire sequence, especially if an entire genome is being sequenced. Another advantage is that the original linkage of the various map positions is maintained throughout the mapping procedure. Alternatively, PCR mapping strategies can be used to map the position of the insertion, using one PCR primer corresponding to a transposon end and one primer corresponding to a known position in the target plasmid. The size of the resultant PCR products allows the insert position and orientation to be determined.

2. Gene mapping by integrative disruption.

Example: A yeast gene has been cloned as part of a large, e.g., 15 kb DNA insert on a plasmid. The investigator wishes to know where, within this 15 kb, the gene is located. The clone was originally isolated by complementation of a mutant phenotype in yeast; hence, a functional assay for the presence of the gene exists. A set of PART insertions is made into the target plasmid and these are then transformed into yeast; non-complementing clones should contain insertions into the gene of interest. A selectable yeast gene (e.g., URA3, TRP1 or HIS3) could be incorporated into the artificial transposon, both simplifying the original selection in yeast for clones maintaining a transposon insertion, and allowing the facile identification of gene disrupter clones which could be later used directly to knock out the gene of interest in the host genome.

3. Introduction of any functional or non-functional DNA cis element, sequence, or combination of sequences into another segment of DNA.

i) Restriction sites for mapping, making deletions, adding new DNA fragments/sequences.

Restriction enzymes are multipurpose tools. By inserting a site for a particular enzyme at a desired location, the site could be used for mapping, making deletions or adding restriction fragments to the target DNA.

Example 1: An artificial transposon containing two Not I restriction sites flanking a selectable marker is inserted into the target plasmid in vitro. Miniprep DNAs are screened by restriction mapping to locate an artificial transposon insertion in the desired region. Alternatively, an insertion library containing artificial transposon insertions throughout the target clone is screened with a junction oligonucleotide to identify an insertion at a particular phosphodiester bond. Once a suitably-positioned transposon is identified, the plasmid is cleaved with Not I, thus removing the majority of the transposon, and generating ends with a Not I restriction site. Since many sites flank the selectable marker in pAT-1 and pAT-2, this approach could be adapted for use with any pair of enzymes that would lead to the removal of the selectable gene and allow the subsequent cloning of an insert at the site. This general approach offers an alternative to creating a restriction endonuclease site by the method of site directed mutagenesis.

Example 2: A yeast artificial chromosome (YAC) containing 800 kb of human DNA is used as a target to generate artificial transposon insertions. Upon recovery of insertions, one is mapped to a position near a site thought to contain no functional genes. Since the artificial transposon contains a single Not I site and the chromosome lacks Not I sites, the unique site could be used to insert a novel gene into this location.

ii) Promoters, enhancers, terminators, introns, exons.

Example: An artificial transposon is created which contains the third exon of gene W which is known to encode a stretch of 99 prolines followed by 33 histidines and then 11 tyrosines. Normal mammalian 5' splice donor, 3' splice acceptor, and branch acceptor sites are incorporated into the transposon at the appropriate positions for correct splicing, along with a selectable marker. The transposon is integrated into gene X on a plasmid, and the plasmid subsequently transfected into mammalian cells in culture. The exon is found to be appropriately incorporated into the transcribed mRNA of gene X, with precise excision of all non-exon sequences. The protein chemistry of the region encoded by this exon is now studied in the new protein context.

iii) Drug-selectable or auxotrophic markers useful in experimental and non-experimental organisms including: bacteria, plants, yeast, insects, Drosophila, worms, rodents, humans, mammals in general. "Marker swap" or "Marker addition" transposons.

Goal: introduce or exchange genetic markers in a vector of interest, using the integration reaction rather than restriction enzymes. Transposons similar to the PART but containing different drug resistance (chloramphenicol, kanamycin) or yeast selectable markers (URA3, TRP1, HIS3, LEU2) between the transposon termini could be integrated into a target plasmid of choice. The resultant plasmids could be selected for the acquisition of the new marker and then if desired, be screened for loss of a pre-existing marker.

Example: You have a plasmid that contains a marker for ampicillin resistance as well as a gene of interest. For an upcoming experiment, you desire that the plasmid contain a chloramphenicol resistance marker, and require that the plasmid be lacking the ampicillin gene. Thus, the end goal is to have a single plasmid carrying your gene of interest, a chloramphenicol resistance marker, and no ampicillin resistance marker. To accomplish this, you perform an in vitro integration with an artificial transposon containing a chloramphenicol gene, and select plasmids that are chloramphenicol resistant. Next, you replica plate to ampicillin-containing plates, and identify chloramphenicol resistant/ ampicillin sensitive clones. The new marker is found to have integrated within the Amp marker.

iv) Genes. Any gene of interest could be cloned into a pAT derivative and directly inserted as a transposon into a DNA target.

Example: A gene therapist wants to build a variety of new adenovirus constructs to test as delivery vehicles for the cystic fibrosis transmembrane regulator (CFTR) gene, which is the human gene responsible for cystic fibrosis. Since both the adenovirus genome and the CFTR cDNA are both quite large, strategies based on restriction enzymes are not easily identified. Instead, the gene therapist clones the CFTR cDNA driven by the CFTR promoter into a pAT derivative carrying a selectable marker, and inserts the resultant artificial transposon carrying the CFTR gene into the adenovirus vector. Thus, various constructs are rapidly built and tested.

v) Any functional or non-functional DNA

DNA segments comprised of any nucleotide sequence or combination of sequences, could be envisioned to be incorporated into an artificial transposon, thus becoming amenable to recombination with a target via an integration reaction.

vi) Codon insertion mutagenesis.

Restriction sites for a rare cutting restriction enzyme (e.g. SrfI, cutting GCCCGGGC) can be positioned just inside the termini of the artificial transposon, but flanking the selectable marker (e.g. dhfr). The restriction sites can be positioned such that, after deletion of the marker-containing (dhfr in the example) SrfI fragment, there would be a net insertion of an integral number of codons into the target plasmid, resulting from the new bases introduced (these would consist of the target site duplication, artificial transposon terminal base pairs, and the restriction site, plus one or two additional base pairs as necessary to ensure the proper reading frame). Following insertion of such an artificial transposon into a target plasmid or cosmid of interest, the population of insertion mutant plasmids or cosmids could be digested en masse with SrfI, diluted and self-ligated. These deleted plasmids would then be retransformed into host cells, resulting in a population of codon insertion mutants. These codon insertion mutants could then be used to study whatever function(s) are encoded in the target DNA biologically. The restriction site would again be very helpful for rapid mapping of the codon insertion. Other methods for codon insertion mutagenesis are taught in the art (33, 34).

4. "Carry along" transposition.

An artificial transposon carries a drug-selectable marker/ or markers which allow selection of transposon-containing DNA target. The transposon also contains other DNA sequences adjacent to the marker (such as a gene). Hence, both the drug marker and the gene of interest are introduced upon integration of an artificial transposon with such a structure.

5. Fusion protein constructs.

An artificial transposon is designed such that, upon insertion into an open reading frame of a functional gene, a fusion protein would be produced. The fusion would be comprised of a portion of the original coding region of the functional gene, as well as a reporter which could be used to identify such active fusion proteins.

Example: An artificial transposon is created that contains the beta galactosidase gene. The reading frame is open from the terminus of the transposon through the beta galactosidase gene. Upon integration in a frame in a target gene, a fusion protein is produced that shows beta galactosidase activity.

6. Transgenic constructs.

A drug-selectable marker useful in the organism under study is introduced into a desired region of a gene or DNA within a cloning vector, for the ultimate purpose of introducing the segment of DNA into the host genome. This general approach has been reported for bacteria, yeast, drosophila, C. elegans, and mouse, as well as other mammals, and includes integrative knockouts such as those reported by M. Capecchi's lab.

Example 1: A researcher wishes to examine a 20 kb segment of mouse DNA for possible promoter activity both in cultured cells and in the context of the organism. An artificial transposon containing a reporter gene such as Chloramphenicol acetyl transferase (CAT), luciferase, or β-galactosidase could be integrated into the 20 kb region, and screened by restriction mapping. Next, the insertions could be tested for expression in cell culture or muscle injection transient assays. Finally, constructs showing expression could be used to generate transgenic animals. Such animals could be used to study the expression conferred by the promoter, by assaying reporter activity in various tissues or developmental states.

Example 2: An artificial transposon is created which contains a human transcriptional enhancer element that functions only in heart muscle tissue during early heart development. By inserting copies of this transposon in the upstream, downstream, and intron regions of a gene of interest (cloned on a plasmid), constructs are generated where the gene would potentially be regulated by the enhancer in a tissue-specific and temporal manner. These constructs are used to generate transgenic animals where this gene would be expressed in this manner.

Example 3: Transgenic knockout constructs. An artificial transposon containing a NEO gene is created and integrated into a plasmid clone carrying the 5' potion of a gene of interest. The insertions are screened, and a single insertion occurring in the first exon of the gene, just downstream of the translation start codon AUG, is identified. The resulting construct is used directly to knockout the gene by generating a transgenic animal by ES technology. A second version would include the addition of a counterselectable marker at the 3' end of the construct to differentiate between homologous and non-homologous insertions. This counterselectable marker could be carded on a second artificial transposon. This general approach has been described by Capecchi and colleagues to generate "knockout mice" lacking the function of a particular gene.

EXAMPLES

Construction of pAT-1 pAT-1 (pSD544) and pAT-2 (pSD545) were constructed as follows. First, the plasmid pRS316 (ref. 15; a derivative of pBLUESCRIPT, Stratagene) was modified to eliminate the ampicillin resistance (amp$^r$) gene. This was accomplished by ligating together two fragments of pRS316 (a 2.1 kb Ssp I fragment and a 2.1 kb Bsa I/Ssp I fragment), thus creating the plasmid pSD528 which lacks a functional bla gene; this plasmid can be propagated in the pyrimidine-requiring E. coli strain MH1066 since the yeast URA3 gene on this construct complements the bacterial pyrF auxotrophy (16). pAT-1 and pAT-2 were constructed from plasmid pSD528 by replacing the pBLUESCRIPT multicloning site (mcs) (from the unique Kpn I site to the unique Sac I site) with polymerase chain reaction (PCR) adapters containing the appropriate sequences to create the structure indicated in FIG. 2. These PCR adapters were generated using primers SD112 (JB661) (5'-AAAA-GCTGGG-TACCGA-ACATGTT-CTCGAGGTCGACGGTATCG-3') (SEQ ID NO:6) and SD113 (JB662) (5'-GCGAATTGGA-GCTCGAAC-ATGTTCACCGC-GGTGG-CGGCCGCTC-3') (SEQ ID NO:7) with plasmids pBLUESCRIPT and pSD511 as templates. The resulting PCR products were digested with Kpn I and Sac I, and ligated to Kpn I/Sac I-digested pSD528 to generate pAT-1 and pAT-2. The structures of these constructs were confirmed by restriction mapping and sequence analysis.

In vitro reaction conditions.

A typical in vitro DNA integration was carried out in a 20 μl reaction volume, and contained the following. 100–500 ng artificial transposon (0.8 kb), 1 μg CsCl-purified plasmid target (a 10 to 1 molar ratio of transposon to target), 2 μl 10 X reaction buffer (150 mM MgCl$_2$, 100 mM Tris HCl, pH 7.5, 100 mM KCl, and 10 mM DTT), 5 μl 20% [w/v] PEG 8000, 2 μl VLPs, and water to 20 μl. The reaction was incubated at 30° Celsius for 30 minutes followed by 37° Celsius for 10 minutes, and then was terminated by adding 1.0 μl 0.5M EDTA and heating to 65° Celsius for 20 minutes. Finally, the nucleic acids were phenol/chloroform extracted, ethanol precipitated, collected by centrifugation, washed with 70% ethanol, and resuspended in 10 μl TE (10 mM Tris, pH 8.0, 1 mM EDTA). 1 μl was used to transform 6 μl DH10B E. coli (Gibco/BRL) to drug resistance by electroporation.

PCR, sequencing, primers, plasmid constructions, CsCl preps.

The PCR was carried out using reagents obtained from Perkin Elmer, as described (17). DNA sequencing was carried out using Sequenase (USB), and analyzed as described (18). Custom oligonucleotide primers were obtained from Operon Technologies, Inc. (Alameda, Calif.). The two primers used for sequencing from within the PART were SD111 (JB563) (5'-GACACTCTGTTATTACAAA TCG-3') (SEQ ID NO:4) and SD110 (JB532) (5'-GGTGATCCCTGAGCAGGTGG-3') (SEQ ID NO:5). The integration site of each PART insertion was determined using either one or both of these primers, and analyzed with the aid of the Wisconsin GCG package. Plasmids were constructed using standard DNA cloning methods (19), and were purified from E. coli cultures by either STET miniprep (20) or alkaline lysis followed by CsCl banding (21).

Preparation of artificial transposons from pAT-1 and derivatives.

20 μg of CsCl-purified plasmid DNA was digested with 50 units of Xmn I (Boehringer Mannhiem) for 4 hours at 37° Celsius. The resulting fragments were separated on a 1% agarose/TBE gel, and the transposon fragment was electroeluted from the gel using an IBI electroelution device.

Recovery of clones carrying transposon insertions using ampicillin/trimethoprim plates.

E. coli clones carrying plasmids with transposon insertions were identified by selection on M9 minimal plates (22) containing 1.0 mM thiamine HCl, 50 μg/ml ampicillin (Amp) and 100 μg/ml trimethoprim (Tri; Sigma). After one to two days incubation at 37° Celsius, the majority of colonies growing on M9/Amp/Tri plates contained plasmids with a transposon insertion. Dilutions of the transformation were routinely plated on LB plates containing 50 μg/ml Amp (22); this control monitored the number of target plasmids successfully carried through the procedure. When compared to the number of colonies on M9/Amp/Tri plates, the frequency of transposon insertion could be estimated (frequency of insertion=[#colonies on M9/Amp/Tri plates]/ [#colonies on LB/Amp plates]). A positive control plasmid, pSD511, containing both Amp$^R$ and Tri$^R$ markers, routinely gave rise to equivalent numbers of colonies on LB/Amp (50 ug/ml), M9/Tri (100 ug/ml), or M9/Amp/Tri (50/100 ug/ml) plates under these conditions.

Transformation of E. coli.

The two strains transformed routinely in this work were DH5α (23) and DH10B (24). DH5α was prepared for electroporation as described (25), and electrocompetent DH10B cells were purchased from Gibco/BRL. Transformation by electroporation was accomplished for both strains using a Biorad Genepulser with 1 mm cuvettes and the following settings: capacitance: 25 μFD; voltage: 1.8 kV; and resistance: 200 ohms. Using pUC19 or pBLUESCRIPT as a test plasmid, freshly-prepared electrocompetent DH5α generally showed transformation efficiencies of $10^7$–$10^8$ colonies/μg DNA, whereas electrocompetent DH10B purchased from BRL/Gibco generally showed efficiencies of $5\times10^8$ to $5\times10^9$ colonies//μg DNA.

VLP preparation.

VLPs were prepared from yeast cultures as described (26). Fractions from the final sucrose gradient containing integrase activity were aliquoted and frozen at −70° Celsius where they were stable for more than 6 months.

In vitro integration of "primer island" transposons into a cloned segment of yeast chromosome III carried on a plasmid target.

We next generated PART insertions in vitro using various plasmid targets. One of the primary test clones consisted of a pRS200 backbone (a derivative of pBLUESCRIPT) with an 8.0 kb insert that spans bp 136,155 to 144,333 of yeast chromosome III; this plasmid is called p76-2. With a single in vitro integration reaction, we recovered approximately 13,000 PART insertions in p76-2 (Table 1).

TABLE 1

Table 1. Recovery of PART insertions into clone 76-2.

| Rxn | EDTA[a] | Total transformants[b] | Total insertion plasmids[c] | Frequency of transposition[d] |
|---|---|---|---|---|
| 1. | − | 0 | 0 | — |
| 2. | − | $3.1 \times 10^8$ | $4.5 \times 10^8$ | — |
| 3. | − | $3.1 \times 10^8$ | $1.3 \times 10^4$ | $4.2 \times 10^{-5}$ |
| 4. | + | $5.7 \times 10^8$ | $5.0 \times 10^2$ | $9.1 \times 10^{-7}$ |

Reaction 1) negative transformation control (no DNA added); 2) positive transformation control (pSD511, which contains both Amp ® and Tri ® markers); 3) complete integration reaction using p76-2 as the target; 4) same as reaction 3, but EDTA was added (inhibits integrase activity).
[a]. +, EDTA added to 25 mM
[b]. Total number of Amp ® transformants
[c]. Total number of Amp ®/Tri ® transformants
[d]. Number of transpositions into target plasmid (Amp ®/Tri ® colonies) divided by the total number of transformants (Amp ® colonies)

By measuring the number of colonies transformed to ampicillin resistance vs. combined trimethoprim and ampicillin resistance, we determined that the frequency of transposon insertion recovery was approximately $4.2\times10^{-5}$ (i.e., 1 insertion per $2.4\times10^4$ target molecules; Table 1). Although this frequency is not likely to represent the upper limits of optimization, it is sufficiently high that a large number of insertion events are readily recovered, while sufficiently low that a single target is generally limited to a single transposon insertion (two transposon insertions in a single target might be useful for some purposes, but would render the molecule useless as a sequencing template).

Analysis of 156 randomly chosen $Amp^R/Tri^R$ colonies indicated that PART insertions occurred into all areas of the plasmid target, including both the pRS200 backbone (6.0 kb) and the 8.0 kb chromosome III insert, as determined by restriction mapping and/or sequence analysis (Table 2).

TABLE 2

Table 2. Examination of Tri ®/Amp ® colonies from a single in vitro integration reaction.

|  |  | % |
|---|---|---|
| Total number of Tri ® clones examined | 156 | 100 |
| # minipreps recovered | 153 | 98 |
| # easily-identifiable insertions | 134 | 86 |
| In insert | 78 | 50 |
| In vector | 56 | 36 |
| Other | 19 | 12 |
| double insertions/cotransformants[a] | 13 | 8 |
| unknown plasmid map | 5 | 3 |
| no transposon | 1 | <1 |

[a]. This class contains some plasmids that apparently had two independent insertions in the target as determined by restriction mapping, and others with DNA sequence that was readable to the insertion junction, at which point two superimposed sequences were observed.

More than 86% of these 156 clones (134) had easily-identifiable PART insertions; of these, 78 (50%)were in the cloned 8 kb insert, while 56 (36%) were in the vector. A small percentage of the clones were found to have two superimposed restriction maps/and or sequences. There are several likely explanations for this result, including the possibility that two plasmids transformed a single E. coli clone, or that two transposon insertions occurred into a single plasmid target; the available evidence indicates that most of these clones are explained by such mechanisms. Hence, a small portion of clones recovered from an in vitro integration reaction would not be suitable for direct DNA sequence analysis for this reason (12% in this example, Table 2). Likewise, vector insertions would not be useful for sequencing the insert. Nevertheless, one of every two $Amp^R/Tri^R$ colonies analyzed from this single reaction could be used directly to obtain DNA sequence from the cloned insert. Furthermore, analysis of only 156 minipreps led to the assembly of 78 useful insertions in an 8 kb insert, corresponding to an expected distribution of roughly one insertion per 100 bp.

The distribution of individual insertions of the artificial transposon relative to adjacent insertions is shown in Table 3.

TABLE 3

Tabulation of PART insertion data from plasmid target p76-2

| Insertion Plasmid | Insertion point in p76.2 (chr III numbering) | distance to 5-prime done |
|---|---|---|
| 5-prime end | 136155 | — |
| 151 | 136394 R | 239 |
| 72 | 136397 F | 3 |
| 25 | 136415 R | 18 |
| 116 | 136425 R | 10 |
| 107 | 136460 R | 35 |
| 93 | 136576 R | 16 |
| 155 | 136611 F | 35 |
| 135 | 136685 F | 74 |
| 46 | 136724 R | 39 |
| 141 | 136767 F | 43 |
| 84 | 136832 R | 65 |
| 33 | 137058 F | 226 |
| 70 | 137165 F | 107 |
| 124 | 137192 R | 27 |
| 101 | 137347 R | 155 |
| 59 | 137451 F | 104 |
| 17 | 137622 R | 171 |
| 77 | 137657 F | 35 |

TABLE 3-continued

Tabulation of PART insertion data from plasmid target p76-2

| | | |
|---|---|---|
| 89 | 137811 F | 154 |
| 147 | 137879 R | 68 |
| 54 | 138127 R | 248 |
| 145 | 138161 F | 34 |
| 105 | 138175 F | 14 |
| 16 | 138263 R | 88 |
| 146 | 138345 F | 82 |
| 20 | 138503 F | 158 |
| 122 | 138581 R | 78 |
| 63 | 138587 F | 6 |
| 125 | 138588 F | 1 |
| 86 | 138618 R | 30 |
| 152 | 138702 F | 84 |
| 110 | 138720 F | 18 |
| 32 | 138747 R | 27 |
| 117 | 138771 F | 24 |
| 114 | 138819 R | 48 |
| 94 | 138905 R | 86 |
| 40 | 138906 R | 1 |
| 112 | 139283 R | 377 |
| 41 | 139291 R | 8 |
| 119 | 139332 R | 41 |
| 102 | 139529 F | 197 |
| 19 | 139551 R | 22 |
| 134 | 139690 R | 139 |
| 85 | 139863 R | 173 |
| 42 | 139980 R | 117 |
| 22 | 140052 R | 72 |
| 73 | 140176 R | 124 |
| 80 | 140259 R | 83 |
| 38 | 140360 F | 101 |
| 90 | 140446 R | 86 |
| 103 | 140794 R | 348 |
| 24 | 141023 R | 229 |
| 57 | 141024 R | 1 |
| 2 | 141074 R | 50 |
| 49 | 141174 F | 100 |
| 11 | 141412 F | 238 |
| 68 | 141633 F | 221 |
| 58 | 141765 F | 132 |
| 12 | 141770 R | 5 |
| 142 | 141836 R | 66 |
| 29 | 141876 F | 40 |
| 69 | 142015 R | 139 |
| 31 | 142027 R | 12 |
| 4 | 142094 R | 67 |
| 78 | 142180 F | 86 |
| 60 | 142226 R | 46 |
| 127 | 142382 R | 156 |
| 3 | 142551 R | 169 |
| 74 | 142713 F | 162 |
| 108 | 142820 F | 107 |
| 6 | 143141 F | 321 |
| 109 | 143165 R | 24 |
| 149 | 143333 R | 168 |
| 27 | 143616 F | 283 |
| 39 | 143856 F | 240 |
| 51 | 143921 F | 65 |
| 13 | 144076 F | 155 |
| 66 | 144127 F | 51 |
| 3-prime end | 144333 | 206 |

Statistics on insertions
n = 78
Mean interval distance = 102.3 +/− 88.1
Insertions/kb for each 1 kb of target:

| Region of target | Number of insertions per kb target DNA |
|---|---|
| 136,155 to 137,000 | 13 |
| 137,000 to 138,000 | 9 |
| 138,000 to 139,000 | 17 |
| 139,000 to 140,000 | 14 |
| 140,000 to 141,000 | 6 |
| 141,000 to 142,000 | 10 |
| 142,000 to 143,000 | 9 |
| 143,000 to 144,000 | 6 |
| 144,000 to 144,333 | 6 |

Mean number of insertions per kb target DNA = 10.2 +/− 3.7

Orientation

Forward 34 (44%)
Reverse 44 (56%)

Since the entire yeast chromosome III sequence has been previously determined (27), we could easily identify the precise sites of transposon integration by determining the nucleotide sequences at the insertion junctions. Indeed, the 78 PART insertions were found to be distributed throughout the entire 8 kb insert (FIG. 3). A little less than half of these insertions were in the forward orientation (34/78 or 44%), indicating a slight orientation bias for this target. However, since primer extensions can be initiated into the sequences flanking the insertion on both sides irrespective of the PART orientation, an orientation bias does not affect the utility of the PART insertion for purposes of DNA sequencing. The mean distance between adjacent insertions was 102.3+/−88.1 overall. Only six of the intervals were greater than 250 bp, and the largest of these was only 377 bp. Hence, the vast majority of the intervals between adjacent transposon insertions were well below the maximum distance that can be reached with an average primer extension under sequencing conditions. A property of Ty1 integrase is that it creates characteristic 5 bp target sequence duplications flanking the insertion site upon integration (10–12, 28). As expected, 5 bp target site duplications were found at each PART integration site examined (only a small portion of the insertions were sequenced at both ends in this example). No deletions or rearrangements were observed.

A conceptual primer extension contig map based on our results is shown in FIG. 4. We have made the assumption that each primer extension would lead to the successful recovery of 250 bp of useful sequence information. 100% of the sequence would be recovered on one strand or the other using the 78 PART insertions shown in FIG. 3. Only 6 gaps (3 on the top strand, and 3 on the bottom; each <150 bp) would exist. But because the two initial primer extensions flanking such a gap would cross in the middle on opposite strands, uninterrupted DNA sequence would be recovered on one strand or the other. Nevertheless, the gaps on the remaining strand could be closed with either: i) additional PART insertions in the necessary regions, identified with appropriate restriction mapping, ii) custom primers, or iii) longer sequencing runs. Of course, we have made the assumption that only 250 bp of sequence information can be recovered from a single primer extension; in fact, greater than 400 is routinely obtained with automated sequencers, and 800 to 1000 is becoming possible with automated sequencers in development. Hence, if the mean readable sequence is extended to 400 bp, 100% of the sequence could be easily recovered using fewer than 78 PART insertions.

Other targets tested.

In addition to clone 76-2 containing a DNA insert from yeast chromosome III, we have tested other plasmid targets. These plasmids had a variety of backbone structures and carded various cloned inserts (Table 3). The backbones included pUC19 and pBLUESCRIPT as well as others, and the DNA inserts originated from different species including yeast and human. In each ease, results similar to those shown for clone 76-2 were obtained: i) insertions were mapped to all regions of these targets, ii) a large number of insertions was readily recovered from reactions using each target, and iii) recovered insertions consistently served as successful sequencing templates. Moreover, in two cases other than p76-2 (pCAR143 and pWAF-1; table 3), this system was used to recover 90–100% of the nucleotide sequence from clones with previously unknown sequences. Hence, in vitro integration of artificial transposons is expected to work well with most or all plasmid targets, making it both a generally useful sequencing tool and a general method of integrating new DNA sequences into plasmid targets to generate recombinant DNA molecules.

MAPPING AND SEQUENCING COSMID DNA USING ARTIFICIAL TRANSPOSONS

We have demonstrated that artificial transposons can be efficiently integrated into a wide variety of plasmid targets in vitro using Ty1 integrase. Our data indicate that cosmids can also serve as targets for integration using the same protocol as that used for plasmids. Hence, DNA mapping, sequencing and functional genetic analysis can be performed directly on large (30–50 kb) DNA inserts propagated in cosmid cloning vectors. These results confirm that the target for artificial transposon insertion is flexible; in principle, any DNA molecule could serve as a target for the integration of artificial transposons in vitro. The resulting recombinant could be used either to analyze the regions surrounding the insertion, or for any other purpose generally provided by recombinant DNA molecules, including but not limited to functional genetic analysis and recombinant DNA engineering.

Supportive Data

1. AT-2 insertions have been generated in four different cosmids using the same methods used to generate AT-2 insertions in plasmids. These include three cosmids obtained from the Lawrence Livermore Genome Center, F23932, F13544, and F20080, each consisting of a Lawrist cloning vector and an insert of approximately 30 to 50 kb derived from Human chromosome 19, as well as one additional cosmid, JEDI-C, also carrying an insert of approximately 30 to 50 kb.

2. Restriction mapping. Insertions mapped to all regions of target cosmids supporting a quasi-random model for integration as was observed for plasmids.

3. AT-2/cosmid recombinants were successfully used as sequencing templates with ABI Prism cycle sequencing technology. More than 100 cosmid recombinants (including 17 from a previously uncharacterized cosmid, F23932) have been evaluated as sequencing templates and the majority (>90%) gave readable sequence of 300 to 600 bp for each primer extension with high levels of accuracy (>95%).

4. 8 kb of previously characterized sequence of the cosmid F13544 was re-analyzed with AT-2 insertions and Prism sequencing technology (see FIG. 11). All available data indicate that this method is fully capable of recovering accurate sequence information comparable with other state-of-the-art methods.

Thus, cosmids can be analyzed with artificial transposon technology at both the structural and sequence levels. It is predicted that cosmid recombinants could also be used for functional genetic analysis. The advantages of direct analysis of DNA inserts propagated as large recombinant cosmid molecules are as follows. 1) Direct analysis allows the original linkage of the insert to be maintained throughout the analysis, avoiding the problems associated with destroying linkage, e.g. as in shotgun sequencing, 2) direct analysis allows the navigation of "difficult" DNA inserts containing complex repeat structures and 3) map and sequence information from a single transposon insertion can be used in concert to permit simplified sequence assembly schemes.

VARYING THE NUCLEOTIDE SEQUENCE AND STRUCTURE OF THE ARTIFICIAL TRANSPOSON

Our initial experiments were performed with the artificial transposon AT-2. Our results suggested that the sequence and design of the artificial transposon were likely to be flexible. We have now tested this hypothesis by designing and constructing artificial transposons with a variety of sequences and features. Like AT-2, these artificial transposons were constructed in pAT-1 or pAT-2 vectors or derivatives (FIG. 12), relying upon the same multicloning site for construction of these plasmids, and the same Xmn I restriction strategy for preparation of the transposon from the vector (in each case, the artificial transposon bears the same relationship to its parent plasmid that AT-2 bears to pAT-2). The results of our studies indicate that, indeed, the sequence of the artificial transposon can be varied substantially while retaining transposition activity. Thus, any desired feature can, in principle, be incorporated into an artificial transposon using methods available for engineering plasmids or linear DNA molecules. The following artificial transposons have been constructed and, where indicated, have also been tested for transposition or otherwise.

1. AT-2. The artificial transposon AT-2 contains at its termini 4 bp of Ty1 U3 terminal sequences (5'-AACA-3'); subterminal primer sites SD110, 111, 118 and 119 used for PCR or sequencing; subterminal restriction sites for mapping and engineering; a drug-selectable dhfr cassette conferring resistance to the antibiotic trimethoprim in E. coli. AT-2 was constructed in the plasmid pAT-2.

2. AT-2-TRP1 This transposon is identical to AT-2 with the exception that the yeast auxotrophic marker TRP 1 has been added at the unique Hind III site present in pAT-2. The overall transposon is approximately 1.6 kb in length. The TRP1 marker is selectable in both bacteria and yeast. AT-2-TRP1 transposes in vitro using the methods established for AT-2. Insertions were found to be quasi-randomly distributed. Following integration into plasmid targets and transformation into yeast, the locations of functionally active regions on the target plasmid were mapped by insertional inactivation. For example, in one plasmid target containing the yeast URA3 and LYS2 genes (pSD553), AT-2-TRP1 insertions were found to inactivate these genes upon insertion within their open reading frames, leading to a Ura- or Lys- phenotype in yeast (Table 4). When insertions occurred outside of these genes in the same target, however, the plasmids were still capable of yielding a Ura+, Lys+ phenotype in yeast. In all cases, a Trp+ phenotype due to the TRP1 marker on the transposon was observed in yeast.

TABLE 4

| AT2-TRP1 /pSD553 recombinants | | | | | |
|---|---|---|---|---|---|
| | Phenotypes | | | | k |
| Recombinant | Amp | Tmp | Ura | Lys | Trp | AT2-TRP1 ins. site |
| 1 | R | R | – | + | + | URA3 ORF |
| 2 | R | R | + | + | + | LYS2 3' UTR |
| 3 | R | R | + | – | + | LYS2 ORF |

TABLE 4-continued

AT2-TRP1/pSD553 recombinants

| Recombinant | Amp | Tmp | Ura | Lys | Trp | AT2-TRP1 ins. site |
|---|---|---|---|---|---|---|
| 4 | R | R | + | + | + | vector (between Amp and CEN) |
| 5 | R | R | + | − | + | ND |
| 6 | R | R | + | − | + | LYS2 ORF |
| 7 | R | R | + | − | + | ND |
| 8 | R | R | + | − | + | ND |
| 9 | R | R | + | + | + | ND |
| 10 | R | R | + | + | + | ND |
| 11 | R | R | + | + | + | ND |
| 12 | R | R | − | + | + | URA3 ORF |
| 13 | R | R | − | + | + | ND |
| 14 | R | R | + | − | + | ND |
| 15 | R | R | + | − | + | ND |
| 16 | R | R | + | + | + | ND |
| 17 | R | R | + | − | + | ND |
| 18 | R | R | + | + | + | ND |
| 19 | R | R | + | + | + | ND |
| 20 | R | R | + | − | + | ND |
| 553 + C | R | S | + | + | − | |
| 554 + C | R | S | − | − | + | |

Legend. Results of functional analysis of pSD553 recombinants in yeast. The results of functional analysis of 20 independent AT-2-TRP1 recombinants of pSD553 are tabulated. The recombinants were first generated in vitro, and recovered in E. coli by selection for trimethoprim resistance. After mapping sites of insertion, each recombinant was transformed into the yeast strain yPH499 (ura352, lys801, trp1D63) and plated on synthetic media lacking uracil, lysine, or tryptophan. Finally, transformants were replica plated to each media and their phenotype scored. R = resistant; S = sensitive; + = growth on media lacking the specified nutrient; − = no growth. The sites of six insertion events determined by sequence analysis are indicated in the last column.

3. AT-2-LacZ. This transposon is identical to AT-2 with the exception that the LacZ marker has been inserted between the unique Sat I and Xho I sites of pAT-2. The overall transposon is approximately 4 kb in length. AT-2-LacZ transposes in vitro with the methods established for AT-2. When insertion occurs in-frame with an open reading frame present on the target, the resulting recombinant encodes a fusion protein which can be assayed for function in the appropriate host using an indicator substrate such as X-gal. We have tested this approach on an 8 kb segment of yeast chromosome III, and AT-2-LacZ accurately predicted the location of a known gene present on the clone. Thus, artificial transposons can be used to functionally map the location of genes by making reporter fusion proteins.

4. AT-2-neo. This transposon is identical to AT-2 with the exception of the addition of a neo cassette at the unique Hind III site in pAT-2. This transposon has not been tested functionally.

5. AT-3. This transposon was derived from pAT-1 by adding a cassette encoding the neo gene at the unique Bam HI site of pAT-1. This neo cassette confers resistance to G418 in yeast and kanamycin in bacteria. AT-3 transposes in vitro with methods established for AT-2. The orientation of the neo cassette is left to right, with the unique Not I site of AT-3 on the left, and the unique Xho I site on the right, of the cassette.

6. AT-4. This transposon is identical to AT-3 with the exception that the neo cassette is in the opposite orientation. AT-4 transposes in vitro with the methods established for AT-3.

7. AT-5. This transposon was designed to contain the bla (ampicillin resistance) gene and is otherwise identical to AT-3. AT-5 has been designed but not built nor tested.

These results collectively indicate that the cis sequences of the artificial transposon can be varied extensively while retaining transposition function and quasi-random integration in vitro. Thus, transposons with custom features can be constructed and used for a variety of purposes. These features include both functional and non-functional DNA sequences, primer sites, restriction sites, and otherwise useful sequences.

REFERENCES

1. Smith, L. M. (1993) Science 262, 530–531.
2. Itakura, K., Rossi, J. J., and Wallace, R. B. (1984) Ann. Rev. Biochem. 53, 323–356.
3. Sambrook, J., Fritch, E. F., and Maniatis, T. (1989) Molecular Cloning A Laboratory Manual, Second Edition. Cold Spring Harbor Laboratory Press, Cold Spring Harbor, N.Y. pp 13.2–13.104.
4. Sulston, J., Du, Z., Thomas, K., Wilson, R., Hillier, L, Staden, R., and etc. (1992) Nature 356, 37–41.
5. Ausubel, F. M., Brent, R., Kingston, R. E., Moore, D. D., Seidman, J. G., Smith, J. A., and Struhl, K. (1989) Current Protocols in Molecular Biology 1, 7.2.1–7.2.20.
6. Strathman, M., Hamilton, B. A., Mayeda, C. A., Simon, M. I., Meyerowitz, E. M., and Palazzolo, M. J. (1991) Proc. Natl. Acad. Sci. USA 88, 1247–1250.
7. Phadnis, S. H., Huang, H. V., and Berg, D. E. (1989) Proc. Natl. Acad. Sci. USA 86, 5908–5912.
8. Way, J. C., Davis, M. A., Morisato, D., Roberts, D. E., and Kleckner, N. (1984) Gene 32, 369–379.
9. Kleckner, N., Bender, J., and Gottesman, S. (1991) Methods Enzymol. 204, 139–180.
9a. Lee, F. Y., Butler, D., and Kleckner, N. (1987) Proc. Natl. Acad. Sci. USA 84, 7876–.
10. Brown, P. O., Bowerman, B., Varmus, H. E., and Bishop, J. M. (1987) Cell 49, 347–356.
11. Eichinger, D. J. and Boeke, J. D. (1988) Cell 54, 955–966.
12. Eichinger, D. J. and Boeke, J. D. (1990) Genes Dev. 4, 324–330.
13. Braiterman, L. and Boeke, J. D. (1994) Mol. Cell. Biol., in press.
14. Braiterman, L. and Boeke, J. D. (1994) Mol. Cell. Biol., in press.
15. Sikorski, R. S., and Hieter, P. (1989) Genetics 122, 19–27.
16. Sikorski, R. S., and Boeke, J. D. (1991) Methods Enzymol. 194, 302–318.
17. Innis, M. A., and Gelfand, D. H. (1990) In: PCR Protocols A Guide to Methods and Applications. Academic Press, Inc., San Diego, Calif. pp 3–12.
18. Sanger, F., Nicklen, S., and Coulson, A. R. (1977) Proc. Natl. Acad. Sci. USA 74, 5463–5467.
19. Sambrook, L., Fritch, E. F., and Maniatis, T. (1989) Molecular Cloning A Laboratory Manual, Second Edition. Cold Spring Harbor Laboratory Press, Cold Spring Harbor, N.Y. pp 1.53–1.110.
20. Holmes, D. S., and Quigley, M. (1981) Anal. Biochem. 114, 193–197.
21. Ausubel, F. M., Brent, R., Kingston, R. E., Moore, D. D., Seidman, J. G., Smith, J. A., and Struhl, K. (1989) Current Protocols in Molecular Biology 1, 1.7.1–1.7.11.
22. Maniatis, T., Fritsch, E. F., and Sambrook, J. (1982) Molecular Cloning A Laboratory Manual. Cold Spring Harbor Laboratory Press, Cold Spring Harbor, N.Y. pp68–69.
23. Hanahan, D. (1983) J. Mol. Biol. 166, 557–580.
24. Calvin, N. M., and Hanawalt, P. C. (1988) J. Bacteriol. 170, 2796–2801.
25. Ausubel, F. M., Brent, R., Kingston, R. E., Moore, D. D., Seidman, J. G., Smith, J. A., and Struhl, K. (1989) Current Protocols in Molecular Biology 1, 1.8.4–1.8.8.

26. Braiterman, L. T., Monakian, G. M., Eichinger, D. J., Merbs, S. L., Gabriel, A., and Boeke, J. D. (1994) *Gene, in press.*
27. Oliver, S. C., van der Aart, Q. J. M., Agostoni-Carbone, M. L., Aigle, M., Alberghina, L., and etc. (1992) *Nature* 357, 38–46.
28. Ji, H., Moore, D. P., Blomberg, M. A., Braiterman, L. T., Voytas, D. F., Natsoulis, G., and Boeke, J. D. (1993) *Cell* 73, 1007–1018.
29. Bushman, F. D., and Craigie, R. (1991) *Proc. Natl. Acad. Sci. USA* 88, 1339–1343.
30. Vora, A. C., McCord, M., Fitzgerald, M. L., Inman, R. B. and Grandgenett, D. P. (1994) *Nucleic Acids. Res.* 22, 4454–4461.
31. Brown, P. O., Singh, I. and Crowley, R. (1995) Genetic Footprinting: using a retroviral integrase to study gene function (abstract). Retroviral Integrases Meeting, Jan. 19, 1995 Washington, D. C.
32. Dyda, F., Hickman, A. B., Jenkins, T. M., Engelman, A., Craigie, R. and Davies, D. R. (1994) *Science* 266, 1981–1986.
33. Barany, F. (1985) *Proc. Natl. Acad. Sci. USA* 82: 4202–4206.
34. Boeke, J. D. (1981) *Molec. Gen. Genet.* 181: 288–191.

We claim:

1. A method for providing templates for DNA sequencing, comprising the steps of:
   incubating in vitro: (1) a population of a target DNA, said target DNA comprising a region of DNA to be sequenced, (2) a retroviral or retrotransposon integrase, and (3) an artificial transposon having two termini which are substrates for said integrase, to form a population of target DNAs with quasi-randomly integrated insertions of the artificial transposon;
   transforming host cells with the population of target DNAs with quasi-randomly integrated insertions of the artificial transposon;
   selecting those host cells which have been transformed with a target DNA with an insertion of the artificial transposon;
   isolating target DNA with an insertion of the artificial transposon from those host cells which have been transformed with a target DNA with an insertion of the artificial transposon, said target DNA with an insertion of the artificial transposon being suitable for use as a DNA sequencing template.

2. The method of claim 1 wherein said integrase is yeast retrotransposon Ty1 integrase.

3. The method of claim 1 wherein said target DNA is a plasmid.

4. The method of claim 1 wherein said target DNA is a cosmid.

5. The method of claim 2 wherein said integrase is supplied as Ty1 virus-like particles.

6. The method of claim 2 wherein each of said termini contains Ty1 U3 sequences.

7. The method of claim 6 wherein said termini consist of 4 to 11 base pairs.

8. The method of claim 1 wherein said artificial transposon is provided by restriction digestion with an enzyme which generates blunt AACA ends.

9. The method of claim 8 wherein said restriction enzyme is XmnI.

10. The method of claim 1 wherein said step of transforming is facilitated by electroporation.

11. The method of claim 1 wherein the molar ratio of artificial transposon to target DNA is at least 2.5:1.

12. A method for sequencing DNA, comprising the steps of:
   incubating in vitro (1) a population of a target DNA, said target DNA comprising a region of DNA to be sequenced, (2) a retrovirus or retrotransposon integrase, and (3) an artificial transposon having two termini which are substrates for said integrase, to form a population of target DNAs with quasi-randomly integrated insertions of the artificial transposon;
   transforming host cells with the population of target DNAs with quasi-randomly integrated insertions of the artificial transposon;
   selecting those host cells which have been transformed with a target DNA with an insertion of the artificial transposon;
   isolating target DNA with an insertion of the artificial transposon from those host cells which have been transformed with a target DNA with an insertion of the artificial transposon, said target DNA with an insertion of the artificial transposon being suitable for use as a DNA sequencing template;
   hybridizing to said isolated target DNA with an insertion of the artificial transposon a primer which is complementary to a portion of the artificial transposon;
   extending said primer to determine a nucleotide sequence of DNA flanking said artificial transposon in said isolated target DNA with an insertion of the artificial transposon.

13. The method of claim 12 wherein said integrase is yeast retrotransposon Ty1 integrase.

14. The method of claim 12 wherein said target DNA is a plasmid.

15. The method of claim 12 wherein said target DNA is a cosmid.

16. The method of claim 13 wherein said integrase is supplied as Ty1 virus-like particles.

17. The method of claim 16 wherein each of said termini is derived from a Ty1 U3 sequence.

18. The method of claim 17 wherein said termini consist of 4 to 11 base pairs.

19. The method of claim 12 wherein said artificial transposon is provided by restriction digestion with an enzyme which generates blunt AACA ends.

20. The method of claim 19 wherein said restriction enzyme is Xmn I.

21. The method of claim 12 wherein the molar ratio of artificial transposon to target DNA is at least 2.5:1.

22. The method of claim 12 wherein said step of transforming is facilitated by electroporation.

23. A method for sequencing DNA, comprising the steps of:

providing a population of target DNAs with quasi-randomly integrated insertions of an artificial transposon, said artificial transposon having termini which are substrates for a retrovirus or a retrotransposon, said population of target DNAs having been formed by: (1) in vitro insertion of said artificial transposon into the target DNAs using a retroviral or retrotransposon integrase; (2) transforming host cells with the population of target DNAs with quasi-randomly integrated insertions of the artificial transposon; (3) selecting those host cells which have been transformed with a target DNA with an insertion of the artificial transposon; and (4) isolating target DNA with an insertion of the artificial transposon from those host cells which have been transformed with a target DNA with an insertion of the artificial transposon;

hybridizing to individual isolated target DNAs of said population a primer which is complementary to a portion of the artificial transposon;

extending said primer to determine a nucleotide sequence of target DNA flanking said artificial transposon.

24. The method of claim 23 wherein the integrase is yeast retrotransposon Ty1 integrase.

25. The method of claim 23 wherein said target DNA is a plasmid.

26. The method of claim 23 wherein said target DNA is a cosmid.

27. The method of claim 24 wherein said integrase is supplied as Ty1 virus-like particles.

28. The method of claim 24 wherein each of said termini is derived from a Ty1 U3 sequence.

29. The method of claim 28 wherein said termini consist of 4 to 11 base pairs.

30. The method of claim 23 wherein the molar ratio of artificial transposon to target DNA is at least 2.5:1.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 4164 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: pAT-1

( x i ) SEQUENCE DESCRIPTION: SEQ ID NO:1:

```
TCGCGCGTTT CGGTGATGAC GGTGAAAACC TCTGACACAT GCAGCTCCCG GAGACGGTCA    60
CAGCTTGTCT GTAAGCGGAT GCCGGGAGCA GACAAGCCCG TCAGGGCGCG TCAGCGGGTG   120
TTGGCGGGTG TCGGGGCTGG CTTAACTATG CGGCATCAGA GCAGATTGTA CTGAGAGTGC   180
ACCATACCAC AGCTTTTCAA TTCAATTCAT CATTTTTTT TTATTCTTTT TTTTGATTTC    240
GGTTTCTTTG AAATTTTTT GATTCGGTAA TCTCCGAACA GAAGGAAGAA CGAAGGAAGG    300
AGCACAGACT TAGATTGGTA TATATACGCA TATGTAGTGT TGAAGAAACA TGAAATTGCC   360
CAGTATTCTT AACCCAACTG CACAGAACAA AAACCTGCAG GAAACGAAGA TAAATCATGT   420
CGAAAGCTAC ATATAAGGAA CGTGCTGCTA CTCATCCTAG TCCTGTTGCT GCCAAGCTAT   480
TTAATATCAT GCACGAAAAG CAAACAAACT TGTGTGCTTC ATTGGATGTT CGTACCACCA   540
AGGAATTACT GGAGTTAGTT GAAGCATTAG GTCCCAAAAT TTGTTTACTA AAAACACATG   600
TGGATATCTT GACTGATTTT TCCATGGAGG GCACAGTTAA GCCGCTAAAG GCATTATCCG   660
CCAAGTACAA TTTTTTACTC TTCGAAGACA GAAAATTTGC TGACATTGGT AATACAGTCA   720
AATTGCAGTA CTCTGCGGGT GTATACAGAA TAGCAGAATG GGCAGACATT ACGAATGCAC   780
ACGGTGTGGT GGGCCCAGGT ATTGTTAGCG GTTTGAAGCA GGCGGCAGAA GAAGTAACAA   840
AGGAACCTAG AGGCCTTTTG ATGTTAGCAG AATTGTCATG CAAGGGCTCC CTATCTACTG   900
GAGAATATAC TAAGGGTACT GTTGACATTG CGAAGAGCGA CAAAGATTTT GTTATCGGCT   960
TTATTGCTCA AAGAGACATG GGTGGAAGAG ATGAAGGTTA CGATTGGTTG ATTATGACAC  1020
CCGGTGTGGG TTTAGATGAC AAGGAGACG CATTGGGTCA ACAGTATAGA ACCGTGGATG  1080
```

```
ATGTGGTCTC TACAGGATCT GACATTATTA TTGTTGGAAG AGGACTATTT GCAAAGGGAA      1140
GGGATGCTAA GGTAGAGGGT GAACGTTACA GAAAAGCAGG CTGGGAAGCA TATTTGAGAA      1200
GATGCGGCCA GCAAAACTAA AAAACTGTAT TATAAGTAAA TGCATGTATA CTAAACTCAC      1260
AAATTAGAGC TTCAATTTAA TTATATCAGT TATTACCCTA TGCGGTGTGA AATACCGCAC      1320
AGATGCGTAA GGAGAAAATA CCGCATCAGG AAATTGTAAA CGTTAATATT TTGTTAAAAT      1380
TCGCGTTAAA TTTTTGTTAA ATCAGCTCAT TTTTAACCA ATAGGCCGAA ATCGGCAAAA       1440
TCCCTTATAA ATCAAAAGAA TAGACCGAGA TAGGGTTGAG TGTTGTTCCA GTTTGGAACA      1500
AGAGTCCACT ATTAAAGAAC GTGGACTCCA ACGTCAAAGG GCGAAAAACC GTCTATCAGG      1560
GCGATGGCCC ACTACGTGAA CCATCACCCT AATCAAGTTT TTTGGGGTCG AGGTGCCGTA      1620
AAGCACTAAA TCGGAACCCT AAAGGGAGCC CCCGATTTAG AGCTTGACGG GGAAAGCCGG      1680
CGAACGTGGC GAGAAAGGAA GGGAAGAAAG CGAAGGAGC GGGCGCTAGG GCGCTGGCAA       1740
GTGTAGCGGT CACGCTGCGC GTAACCACCA CACCCGCCGC GCTTAATGCG CCGCTACAGG      1800
GCGCGTCGCG CCATTCGCCA TTCAGGCTGC GCAACTGTTG GGAAGGGCGA TCGGTGCGGG     1860
CCTCTTCGCT ATTACGCCAG CTGGCGAAAG GGGGATGTGC TGCAAGGCGA TTAAGTTGGG     1920
TAACGCCAGG GTTTTCCCAG TCACGACGTT GTAAAACGAC GGCCAGTGAA TTGTAATACG     1980
ACTCACTATA GGGCGAATTG GAGCTCGAAC ATGTTCACCG CGGTGGCGGC CGCTCTAGAA     2040
CTAGTGGATC CCCCGGGCTG CAGGAATTCG ATATCAAGCT TATCGATACC GTCGACCTCG     2100
AGAACATGTT CGGTACCAGC TTTTGTTCCC TTTAGTGAGG GTTAATTCCG AGCTTGGCGT     2160
AATCATGGTC ATAGCTGTTT CCTGTGTGAA ATTGTTATCC GCTCACAATT CCACACAACA     2220
TACGAGCCGG AAGCATAAAG TGTAAAGCCT GGGGTGCCTA ATGAGTGAGG TAACTCACAT     2280
TAATTGCGTT GCGCTCACTG CCCGCTTTCC AGTCGGGAAA CCTGTCGTGC CAGCTGCATT     2340
AATGAATCGG CCAACGCGCG GGGAGAGGCG GTTTGCGTAT TGGGCGCTCT TCCGCTTCCT     2400
CGCTCACTGA CTCGCTGCGC TCGGTCGTTC GGCTGCGGCG AGCGGTATCA GCTCACTCAA     2460
AGGCGGTAAT ACGGTTATCC ACAGAATCAG GGGATAACGC AGGAAAGAAC ATGTGAGCAA     2520
AAGGCCAGCA AAAGGCCAGG AACCGTAAAA AGGCCGCGTT GCTGGCGTTT TTCCATAGGC     2580
TCCGCCCCCC TGACGAGCAT CACAAAAATC GACGCTCAAG TCAGAGGTGG CGAAACCCGA     2640
CAGGACTATA AAGATACCAG GCGTTTCCCC CTGGAAGCTC CCTCGTGCGC TCTCCTGTTC     2700
CGACCCTGCC GCTTACCGGA TACCTGTCCG CCTTTCTCCC TTCGGGAAGC GTGGCGCTTT     2760
CTCATAGCTC ACGCTGTAGG TATCTCAGTT CGGTGTAGGT CGTTCGCTCC AAGCTGGGCT     2820
GTGTGCACGA ACCCCCCGTT CAGCCCGACC GCTGCGCCTT ATCCGGTAAC TATCGTCTTG     2880
AGTCCAACCC GGTAAGACAC GACTTATCGC CACTGGCAGC AGCCACTGGT AACAGGATTA     2940
GCAGAGCGAG GTATGTAGGC GGTGCTACAG AGTTCTTGAA GTGGTGGCCT AACTACGGCT     3000
ACACTAGAAG GACAGTATTT GGTATCTGCG CTCTGCTGAA GCCAGTTACC TTCGGAAAAA     3060
GAGTTGGTAG CTCTTGATCC GGCAAACAAA CCACCGCTGG TAGCGGTGGT TTTTTTGTTT     3120
GCAAGCAGCA GATTACGCGC AGAAAAAAAG GATCTCAAGA AGATCCTTTG ATCTTTTCTA     3180
CGGGGTCTGA CGCTCAGTGG AACGAAAACT CACGTTAAGG GATTTTGGTC ATGAGATTAT     3240
CAAAAAGGAT CTTCACCTAG ATCCTTTTAA ATTAAAAATG AAGTTTTAAA TCAATCTAAA     3300
GTATATATGA GTAAACTTGG TCTGACAGTT ACCAATGCTT AATCAGTGAG GCACCTATCT     3360
CAGCGATCTG TCTATTTCGT TCATCCATAG TTGCCTGACT CCCCGTCGTG TAGATAACTA     3420
CGATACGGGA GGGCTTACCA TCTGGCCCCA GTGCTGCAAT GATACCGATT ATTGAAGCAT     3480
```

-continued

```
TTATCAGGGT TATTGTCTCA TGAGCGGATA CATATTTGAA TGTATTTAGA AAAATAAACA    3540
AATAGGGGTT CCGCGCACAT TTCCCCGAAA AGTGCCACCT GGGTCCTTTT CATCACGTGC    3600
TATAAAAATA ATTATAATTT AAATTTTTTA ATATAAATAT ATAAATTAAA AATAGAAAGT    3660
AAAAAAAGAA ATTAAAGAAA AAATAGTTTT TGTTTCCGA  AGATGTAAAA GACTCTAGGG    3720
GGATCGCCAA CAAATACTAC CTTTTATCTT GCTCTTCCTG CTCTCAGGTA TTAATGCCGA    3780
ATTGTTTCAT CTTGTCTGTG TAGAAGACCA CACACGAAAA TCCTGTGATT TTACATTTTA    3840
CTTATCGTTA ATCGAATGTA TATCTATTTA ATCTGCTTTT CTTGTCTAAT AAATATATAT    3900
GTAAAGTACG CTTTTGTTG  AAATTTTTA  AACCTTTGTT TATTTTTTT  TCTTCATTCC    3960
GTAACTCTTC TACCTTCTTT ATTTACTTTC TAAAATCCAA ATACAAAACA TAAAAATAAA    4020
TAAACACAGA GTAAATTCCC AAATTATTCC ATCATTAAAA GATACGAGGC GCGTGTAAGT    4080
TACAGGCAAG CGATCCGTCC TAAGAAACCA TTATTATCAT GACATTAACC TATAAAAATA    4140
GGCGTATCAC GAGGCCCTTT CGTC                                          4164
```

( 2 ) INFORMATION FOR SEQ ID NO:2:

( i ) SEQUENCE CHARACTERISTICS:
        ( A ) LENGTH: 4933 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: pAT-2

( x i ) SEQUENCE DESCRIPTION: SEQ ID NO:2:

```
TCGCGCGTTT CGGTGATGAC GGTGAAAACC TCTGACACAT GCAGCTCCCG GAGACGGTCA      60
CAGCTTGTCT GTAAGCGGAT GCCGGGAGCA GACAAGCCCG TCAGGGCGCG TCAGCGGGTG     120
TTGGCGGGTG TCGGGGCTGG CTTAACTATG CGGCATCAGA GCAGATTGTA CTGAGAGTGC     180
ACCATACCAC AGCTTTTCAA TTCAATTCAT CATTTTTTT  TTATTCTTTT TTTTGATTTC     240
GGTTTCTTTG AAATTTTTTT GATTCGGTAA TCTCCGAACA GAAGGAAGAA CGAAGGAAGG     300
AGCACAGACT TAGATTGGTA TATATACGCA TATGTAGTGT TGAAGAAACA TGAAATTGCC     360
CAGTATTCTT AACCCAACTG CACAGAACAA AAACCTGCAG GAAACGAAGA TAAATCATGT     420
CGAAAGCTAC ATATAAGGAA CGTGCTGCTA CTCATCCTAG TCCTGTTGCT GCCAAGCTAT     480
TTAATATCAT GCACGAAAAG CAAACAAACT TGTGTGCTTC ATTGGATGTT CGTACCACCA     540
AGGAATTACT GGAGTTAGTT GAAGCATTAG GTCCAAAAAT TTGTTTACTA AAAACACATG     600
TGGATATCTT GACTGATTTT TCCATGGAGG GCACAGTTAA GCCGCTAAAG GCATTATCCG     660
CCAAGTACAA TTTTTTACTC TTCGAAGACA GAAAATTTGC TGACATTGGT AATACAGTCA     720
AATTGCAGTA CTCTGCGGGT GTATACAGAA TAGCAGAATG GGCAGACATT ACGAATGCAC     780
ACGGTGTGGT GGGCCCAGGT ATTGTTAGCG GTTGAAGCA  GGCGGCAGAA GAAGTAACAA     840
AGGAACCTAG AGGCCTTTTG ATGTTAGCAG AATTGTCATG CAAGGGCTCC CTATCTACTG     900
GAGAATATAC TAAGGGTACT GTTGACATTG CGAAGAGCGA CAAAGATTTT GTTATCGGCT     960
TTATTGCTCA AAGAGACATG GGTGGAAGAG ATGAAGGTTA CGATTGGTTG ATTATGACAC    1020
CCGGTGTGGG TTTAGATGAC AAGGGAGACG CATTGGGTCA ACAGTATAGA ACCGTGGATG    1080
```

```
ATGTGGTCTC TACAGGATCT GACATTATTA TTGTTGGAAG AGGACTATTT GCAAAGGGAA   1140
GGGATGCTAA GGTAGAGGGT GAACGTTACA GAAAAGCAGG CTGGGAAGCA TATTTGAGAA   1200
GATGCGGCCA GCAAAACTAA AAAACTGTAT TATAAGTAAA TGCATGTATA CTAAACTCAC   1260
AAATTAGAGC TTCAATTTAA TTATATCAGT TATTACCCTA TGCGGTGTGA AATACCGCAC   1320
AGATGCGTAA GGAGAAAATA CCGCATCAGG AAATTGTAAA CGTTAATATT TTGTTAAAAT   1380
TCGCGTTAAA TTTTTGTTAA ATCAGCTCAT TTTTTAACCA ATAGGCCGAA ATCGGCAAAA   1440
TCCCTTATAA ATCAAAAGAA TAGACCGAGA TAGGGTTGAG TGTTGTTCCA GTTGGAACA    1500
AGAGTCCACT ATTAAAGAAC GTGGACTCCA ACGTCAAAGG GCGAAAAACC GTCTATCAGG   1560
GCGATGGCCC ACTACGTGAA CCATCACCCT AATCAAGTTT TTTGGGGTCG AGGTGCCGTA   1620
AAGCACTAAA TCGGAACCCT AAAGGGAGCC CCCGATTTAG AGCTTGACGG GGAAAGCCGG   1680
CGAACGTGGC GAGAAAGGAA GGGAAGAAAG CGAAAGGAGC GGGCGCTAGG GCGCTGGCAA   1740
GTGTAGCGGT CACGCTGCGC GTAACCACCA CACCCGCCGC GCTTAATGCG CCGCTACAGG   1800
GCGCGTCGCG CCATTCGCCA TTCAGGCTGC GCAACTGTTG GGAAGGGCGA TCGGTGCGGG   1860
CCTCTTCGCT ATTACGCCAG CTGGCGAAAG GGGGATGTGC TGCAAGGCGA TTAAGTTGGG   1920
TAACGCCAGG GTTTTCCCAG TCACGACGTT GTAAAACGAC GGCCAGTGAA TTGTAATACG   1980
ACTCACTATA GGGCGAATTG GAGCTCGAAC ATGTTCACCG CGGTGGCGGC CGCTCTAGAA   2040
CTAGTGGATC CTGCAAGCAG GATAGACGGC ATGCACGATT TGTAATAACA GAGTGTCTTG   2100
TATTTTTAAA GAAAGTCTAT TTAATACAAG TGATTATATT AATAACGGT AAGCATCAGC    2160
GGGTGACAAA ACGAGCATGC TTACTAATAA AATGTTAACC TCTGAGGAAG AATTGTGAAA   2220
CTATCACTAA TGGTAGCTAT ATCGAAGAAT GGAGTTATCG GGAATGGCCC TGATATTCCA   2280
TGGAGTGCCA AAGGTGAACA GCTCCTGTTT AAAGCTATTA CCTATAACCA ATGGCTGTTG   2340
GTTGGACGCA AGACTTTTGA ATCAATGGGA GCATTACCCA ACCGAAAGTA TGCGGTCGTA   2400
ACACGTTCAA GTTTTACATC TGACAATGAG AACGTATTGA TCTTTCCATC AATTAAAGAT   2460
GCTTTAACCA ACCTAAAGAA AATAACGGAT CATGTCATTG TTTCAGGTGG TGGGAGATA    2520
TACAAAAGCC TGATCGATCA AGTAGATACA CTACATATAT CTACAATAGA CATCGAGCCG   2580
GAAGGTGATG TTTACTTTCC TGAAATCCCC AGCAATTTTA GGCCAGTTTT TACCCAAGAC   2640
TTCGCCTCTA ACATAAATTA TAGTTACCAA ATCTGGCAAA AGGGTTAACA AGTGGCAGCA   2700
ACGGATTCGC AAACCTGTCA CGCCTTTTGT GCCAAAAGCC GCGCCAGGTT GCGATCCGC    2760
TGTGCCAGGC GTTAGGCGTC ATATGAAGAT TTCGGTGATC CCTGAGCAGG TGGCGGAAAC   2820
ATTGGATGCT GAGAATTCGA TATCAAGCTT ATCGATACCG TCGACCTCGA GAACATGTTC   2880
GGTACCAGCT TTTGTTCCCT TTAGTGAGGG TTAATTCCGA GCTTGGCGTA ATCATGGTCA   2940
TAGCTGTTTC CTGTGTGAAA TTGTTATCCG CTCACAATTC CACACAACAT ACGAGCCGGA   3000
AGCATAAAGT GTAAAGCCTG GGGTGCCTAA TGAGTGAGGT AACTCACATT AATTGCGTTG   3060
CGCTCACTGC CCGCTTTCCA GTCGGGAAAC CTGTCGTGCC AGCTGCATTA ATGAATCGGC   3120
CAACGCGCGG GGAGAGGCGG TTTGCGTATT GGGCGCTCTT CCGCTTCCTC GCTCACTGAC   3180
TCGCTGCGCT CGGTCGTTCG GCTGCGGCGA GCGGTATCAG CTCACTCAAA GGCGGTAATA   3240
CGGTTATCCA CAGAATCAGG GGATAACGCA GGAAAGAACA TGTGAGCAAA AGGCCAGCAA   3300
AAGGCCAGGA ACCGTAAAAA GGCCGCGTTG CTGGCGTTTT TCCATAGGCT CCGCCCCCCT   3360
GACGAGCATC ACAAAAATCG ACGCTCAAGT CAGAGGTGGC GAAACCCGAC AGGACTATAA   3420
AGATACCAGG CGTTTCCCCC TGGAAGCTCC CTCGTGCGCT CTCCTGTTCC GACCCTGCCG   3480
```

```
CTTACCGGAT ACCTGTCCGC CTTTCTCCCT TCGGGAAGCG TGGCGCTTTC TCATAGCTCA      3540
CGCTGTAGGT ATCTCAGTTC GGTGTAGGTC GTTCGCTCCA AGCTGGGCTG TGTGCACGAA      3600
CCCCCCGTTC AGCCCGACCG CTGCGCCTTA TCCGGTAACT ATCGTCTTGA GTCCAACCCG      3660
GTAAGACACG ACTTATCGCC ACTGGCAGCA GCCACTGGTA ACAGGATTAG CAGAGCGAGG      3720
TATGTAGGCG GTGCTACAGA GTTCTTGAAG TGGTGGCCTA ACTACGGCTA CACTAGAAGG      3780
ACAGTATTTG GTATCTGCGC TCTGCTGAAG CCAGTTACCT TCGGAAAAAG AGTTGGTAGC      3840
TCTTGATCCG GCAAACAAAC CACCGCTGGT AGCGGTGGTT TTTTGTTTG CAAGCAGCAG       3900
ATTACGCGCA GAAAAAAGG ATCTCAAGAA GATCCTTTGA TCTTTTCTAC GGGGTCTGAC       3960
GCTCAGTGGA ACGAAAACTC ACGTTAAGGG ATTTTGGTCA TGAGATTATC AAAAAGGATC      4020
TTCACCTAGA TCCTTTTAAA TTAAAAATGA AGTTTTAAAT CAATCTAAAG TATATATGAG      4080
TAAACTTGGT CTGACAGTTA CCAATGCTTA ATCAGTGAGG CACCTATCTC AGCGATCTGT      4140
CTATTTCGTT CATCCATAGT TGCCTGACTC CCCGTCGTGT AGATAACTAC GATACGGGAG      4200
GGCTTACCAT CTGGCCCCAG TGCTGCAATG ATACCGATTA TTGAAGCATT TATCAGGGTT      4260
ATTGTCTCAT GAGCGGATAC ATATTTGAAT GTATTAGAA AAATAAACAA ATAGGGGTTC       4320
CGCGCACATT TCCCCGAAAA GTGCCACCTG GGTCCTTTTC ATCACGTGCT ATAAAATAA       4380
TTATAATTTA AATTTTTTAA TATAAATATA TAAATTAAAA ATAGAAAGTA AAAAAGAAA       4440
TTAAAGAAAA AATAGTTTTT GTTTTCCGAA GATGTAAAAG ACTCTAGGGG GATCGCCAAC      4500
AAATACTACC TTTTATCTTG CTCTTCCTGC TCTCAGGTAT TAATGCCGAA TTGTTTCATC      4560
TTGTCTGTGT AGAAGACCAC ACACGAAAAT CCTGTGATTT ACATTTTAC TTATCGTTAA       4620
TCGAATGTAT ATCTATTTAA TCTGCTTTTC TTGTCTAATA AATATATATG TAAAGTACGC      4680
TTTTTGTTGA AATTTTTTAA ACCTTTGTTT ATTTTTTTT CTTCATTCCG TAACTCTTCT       4740
ACCTTCTTTA TTTACTTTCT AAAATCCAAA TACAAAACAT AAAATAAAT AAACACAGAG       4800
TAAATTCCCA AATTATTCCA TCATTAAAAG ATACGAGGCG CGTGTAAGTT ACAGGCAAGC      4860
GATCCGTCCT AAGAAACCAT TATTATCATG ACATTAACCT ATAAAAATAG GCGTATCACG      4920
AGGCCCTTTC GTC                                                         4933
```

( 2 ) INFORMATION FOR SEQ ID NO:3:

( i ) SEQUENCE CHARACTERISTICS:
        ( A ) LENGTH: 864 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: PART ( x i ) SEQUENCE DESCRIPTION: SEQ ID NO:3:

```
TGTTCACCGC GGTGGCGGCC GCTCTAGAAC TAGTGGATCC TGCAAGCAGG ATAGACGGCA        60
TGCACGATTT GTAATAACAG AGTGTCTTGT ATTTTAAAG AAAGTCTATT TAATACAAGT        120
GATTATATTA ATAACGGTA AGCATCAGCG GGTGACAAAA CGAGCATGCT TACTAATAAA        180
ATGTTAACCT CTGAGGAAGA ATTGTGAAAC TATCACTAAT GGTAGCTATA TCGAAGAATG       240
GAGTTATCGG GAATGGCCCT GATATTCCAT GGAGTGCCAA AGGTGAACAG CTCCTGTTTA       300
```

```
AAGCTATTAC CTATAACCAA TGGCTGTTGG TTGGACGCAA GACTTTTGAA TCAATGGGAG      360

CATTACCCAA CCGAAAGTAT GCGGTCGTAA CACGTTCAAG TTTTACATCT GACAATGAGA      420

ACGTATTGAT CTTTCCATCA ATTAAAGATG CTTTAACCAA CCTAAAGAAA ATAACGGATC      480

ATGTCATTGT TTCAGGTGGT GGGGAGATAT ACAAAAGCCT GATCGATCAA GTAGATACAC      540

TACATATATC TACAATAGAC ATCGAGCCGG AAGGTGATGT TTACTTTCCT GAAATCCCCA      600

GCAATTTTAG GCCAGTTTTT ACCCAAGACT TCGCCTCTAA CATAAATTAT AGTTACCAAA      660

TCTGGCAAAA GGGTTAACAA GTGGCAGCAA CGGATTCGCA AACCTGTCAC GCCTTTTGTG      720

CCAAAAGCCG CGCCAGGTTT GCGATCCGCT GTGCCAGGCG TTAGGCGTCA TATGAAGATT      780

TCGGTGATCC CTGAGCAGGT GGCGGAAACA TTGGATGCTG AGAATTCGAT ATCAAGCTTA      840

TCGATACCGT CGACCTCGAG AACA                                            864
```

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: JB563

( x i ) SEQUENCE DESCRIPTION: SEQ ID NO:4:

```
GACACTCTGT TATTACAAAT CG                                              22
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: JB532

( x i ) SEQUENCE DESCRIPTION: SEQ ID NO:5:

```
GGTGATCCCT GAGCAGGTGG                                                 20
```

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO (vii) IMMEDIATE SOURCE:
    (B) CLONE: JB661

(xi) SEQUENCE DESCRIPTION: SEQ ID NO:6:

AAAAGCTGGG TACCGAACAT GTTCTCGAGG TCGACGGTAT CG        42

(2) INFORMATION FOR SEQ ID NO:7:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: JB662

(xi) SEQUENCE DESCRIPTION: SEQ ID NO:7:

GCGAATTGGA GCTCGAACAT GTTCACCGCG GTGGCGGCCG CTC        43